US011891645B2

(12) United States Patent
Klitgaard et al.

(10) Patent No.: US 11,891,645 B2
(45) Date of Patent: Feb. 6, 2024

(54) SERINE PROTEASE VARIANTS AND POLYNUCLEOTIDES ENCODING SAME

(71) Applicant: NOVOZYMES A/S, Bagsvaerd (DK)

(72) Inventors: Dorte M. K. Klitgaard, Bagsvaerd (DK); Roland Alexander Pache, Valby (DK); Martin Gudman, Holte (DK); Anders G. Sandström, Södra Sandby (SE)

(73) Assignee: NOVOZYMES A/S, Bagsvaerd (DK)

( * ) Notice: Subject to any disclaimer, the term of this patent is extended or adjusted under 35 U.S.C. 154(b) by 1417 days.

(21) Appl. No.: 16/318,509

(22) PCT Filed: Jul. 14, 2017

(86) PCT No.: PCT/EP2017/067881
§ 371 (c)(1),
(2) Date: Jan. 17, 2019

(87) PCT Pub. No.: WO2018/015303
PCT Pub. Date: Jan. 25, 2018

(65) Prior Publication Data
US 2023/0193327 A1  Jun. 22, 2023

(30) Foreign Application Priority Data

Jul. 21, 2016 (EP) .................... 16180498
Oct. 21, 2016 (EP) .................... 16195087

(51) Int. Cl.
C12N 7/06 (2006.01)
C12N 7/00 (2006.01)
C12N 9/58 (2006.01)
C12N 9/50 (2006.01)
C12P 7/10 (2006.01)

(52) U.S. Cl.
CPC .................. *C12P 7/10* (2013.01); *C12N 9/58* (2013.01); *C12Y 304/21* (2013.01)

(58) Field of Classification Search
CPC ..... C12P 7/06; C12P 7/00; C12N 9/58; C12N 9/50; C12Y 304/21
See application file for complete search history.

(56) References Cited

U.S. PATENT DOCUMENTS

| 5,231,017 | A | 7/1993 | Lantero |
| 5,321,017 | A | 6/1994 | Golub et al. |
| 10,927,361 | B2 | 2/2021 | Ayabe et al. |
| 2011/0143410 | A1 | 6/2011 | Soong et al. |
| 2015/0259662 | A1* | 9/2015 | Stringer ................ A23K 40/25 435/68.1 |
| 2018/0340191 | A1 | 11/2018 | Kreel |

FOREIGN PATENT DOCUMENTS

| EP | 3487995 B1 | 5/2021 |
| WO | 2003/066826 A2 | 8/2003 |
| WO | 2007/145912 A1 | 12/2007 |
| WO | 2011072191 A2 | 6/2011 |
| WO | 2014/037438 A1 | 3/2014 |
| WO | 2015/197871 A1 | 12/2015 |
| WO | 2017/050291 A1 | 3/2017 |

OTHER PUBLICATIONS

FLOUDAS_2014_XP_008037111.1_Alignment_with_SID3.
WO—2014037438A1—Stringer et al., 2014, SID24 alignment with SID3.
Cong, 2015, Chinese doctoral dissertation full text database, Basic Science Series, 3—Incl EnAb—(CN OA).
Liu, 2012, Chinese Excellent Doctoral Dissertation full text database, Agricultural Science Series 2—Incl EnAb—(CN OA).
Zhang et al, 2015, Applied and environmental microbiology 81(18), 1-30—(CN OA).
Ditursi et al, 2006, Protein Engineering 19(11), 517-524.
WO 2014-037438 A1—EBI Accession No. BBD62623.

* cited by examiner

*Primary Examiner* — Maryam Monshipouri
(74) *Attorney, Agent, or Firm* — David A. Fazzolare

(57) ABSTRACT

The present invention relates to serine protease variants, having improved properties compared to the parent protease, in particular variants of a serine protease derived from a strain of *Meripilus giganteus* belonging to the S53 family. The varinats according to the invention have in particular increased stability, e.g., increased thermo-stability, increased specific activity, and/or increased expression levels, compared to the parent protease. The present invention also relates to polynucleotides encoding the variants; nucleic acid constructs, vectors, and host cells comprising the polynucleotides; and methods of using the variants.

35 Claims, No Drawings
Specification includes a Sequence Listing.

SERINE PROTEASE VARIANTS AND POLYNUCLEOTIDES ENCODING SAME

CROSS-REFERENCE TO RELATED APPLICATIONS

This application is a 35 U.S.C. 371 national application of international application no. PCT/EP2017/067881 filed Jul. 14, 2017, which claims priority or the benefit under 35 U.S.C. 119 of European application nos. 16180498.4 and 16195087.8, filed Jul. 21, 2016 and Oct. 21, 2016, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Production of fermentation products, such as ethanol, from starch-containing material is well-known in the art. Generally two different kinds of processes are used. The most commonly used process, often referred to as a "conventional process", includes liquefying gelatinized starch at high temperature using typically a bacterial alpha-amylase, followed by simultaneous saccharification and fermentation carried out in the presence of a glucoamylase and a fermenting organism. Another well-known process, often referred to as a "raw starch hydrolysis"-process (RSH process) includes simultaneously saccharifying and fermenting granular starch below the initial gelatinization temperature typically in the presence of an acid fungal alpha-amylase and a glucoamylase.

U.S. Pat. No. 5,231,017-A discloses the use of an acid fungal protease during ethanol fermentation in a process comprising liquefying gelatinized starch with an alpha-amylase.

WO 2003/066826 discloses a raw starch hydrolysis process (RSH process) carried out on non-cooked mash in the presence of fungal glucoamylase, alpha-amylase and fungal protease.

WO 2007/145912 discloses a process for producing ethanol comprising contacting a slurry comprising granular starch obtained from plant material with an alpha-amylase capable of solubilizing granular starch at a pH of 3.5 to 7.0 and at a temperature below the starch gelatinization temperature for a period of 5 minutes to 24 hours; obtaining a substrate comprising greater than 20% glucose, and fermenting the substrate in the presence of a fermenting organism and starch hydrolyzing enzymes at a temperature between 10° C. and 40° C. for a period of 10 hours to 250 hours. Additional enzymes added during the contacting step may include protease.

WO 2014/037438 discloses serine proteases derived from *Meripilus giganteus, Trametes versicolor,* and *Dichomitus squalens* and their use in animal feed.

It is an object of the present invention to identify variants of the *M. giganteus* S53 proteases that will result in an increased storage stability (e.g., increased thermos-stability), and improved expression yield of the variant protease compared to the wild type parent enzyme.

The present invention provides protease variants with improved properties compared to its parent.

SUMMARY OF THE INVENTION

In a first aspect the present invention relates to protease variants, comprising a substitution at one or more positions corresponding to positions 1, 5, 9, 25, 29, 30, 32, 38, 39, 40, 41, 42, 45, 46, 49, 50, 53, 54, 55, 57, 59, 60, 61, 62, 64, 67, 68, 69, 74, 76, 77, 78, 79, 80, 81, 82, 87, 93, 94, 96, 99, 102, 103, 105, 109, 111, 112, 114, 115, 117, 122, 123, 124, 128, 130, 136, 141, 142, 145, 146, 147, 150, 153, 154, 157, 159, 161,167, 169, 175, 182, 185, 199, 200, 205, 207, 209, 210, 213, 216, 217, 225, 228, 231, 234, 237, 242, 244, 245, 246, 248, 258, 262, 266, 267, 269, 271, 272, 276, 278, 280, 284, 289, 293, 296, 299, 305, 308, 313, 314, 317, 318, 319, 321, 322, 324, 325, 326, 329, 330, 331, 333, 336, 338, 341, 343, 345, 347, 348, 355, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased thermo-stability measured as improvement factor, HIF, compared to the protease of SEQ ID NO: 3.

In a second aspect the present invention relates to protease variants, comprising a substitution at one or more positions corresponding to positions 20, 27, 29, 34, 40, 42, 45, 46, 50, 53, 54, 55, 58, 59, 60, 61, 62, 66, 69, 76, 81, 87, 93, 96, 98, 101, 102, 103, 109, 110, 115, 117, 122, 124, 125, 127, 128, 130, 136, 141, 142, 145, 146, 148, 149, 150, 153, 154, 157, 159, 161, 164, 167, 182, 183, 184, 185, 188, 199, 200, 207, 208, 209, 210, 211, 213, 216, 219, 228, 231, 237, 244, 249, 252, 253, 261, 266, 267, 272, 275, 276, 277, 280, 285, 288, 291, 292, 293, 294, 296, 299, 303, 304, 305, 306, 307, 308, 310, 317, 318, 319, 321, 326, 327, 336, 338, 341, 344, 345, 348, 356, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased specific activity measured as improvement factor, AIF, compared to the protease of SEQ ID NO: 3.

In a third aspect the present invention relates to protease variants, comprising a substitution at one or more positions corresponding to positions 2, 17, 22, 41, 41, 42, 45, 46, 54, 55, 57, 59, 60, 61, 62, 63, 64, 66, 69, 80, 82, 84, 87, 98, 99, 102, 103, 112, 114, 115, 129, 131, 134, 149, 159, 167, 169, 199, 200, 205, 207, 209, 211, 213, 217,242, 250, 266, 267, 269, 270, 271, 272, 274, 278, 279, 280, 284, 288, 291, 292, 294, 296, 301, 307, 314, 329, 331, 333, 336, 362, and 363 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased expression level measured as improvement factor, EIF, compared to the protease of SEQ ID NO: 3.

The present invention also relates to polynucleotides encoding the variants; nucleic acid constructs, vectors, and host cells comprising the polynucleotides; and methods of producing the variants. In a further aspect the present invention relates to compositions comprising the variants of the invention.

The present invention also relates to a process for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a variant protease. In another aspect the present invention relates to a process for producing a fermentation product from starch-containing material comprising the steps of:
(a) liquefying starch-containing material in the presence of an alpha-amylase;
(b) saccharifying the liquefied material obtained in step (a) using a glucoamylse;
(c) fermenting using a fermenting organism;
wherein a variant protease of the invention is present during step b) and/or c).

Definitions

Protease: The term "protease" (also designated peptidases, proteinases, peptide hydrolases, or proteolytic enzymes) means a proteolytic activity (EC 3.4) that catalyzes the cleavage of peptide bonds. For purposes of the present invention, serine protease activity is determined according to the procedure described in the Examples. In one aspect, the variants of the present invention have at least 20%, e.g., at least 40%, at least 50%, at least 60%, at least 70%, at least 80%, at least 90%, at least 95%, or at least 100% of the protease activity of the mature polypeptide of SEQ ID NO: 2.

Protease activity: The term "protease activity" means proteolytic activity (EC 3.4). There are several protease activity types such as trypsin-like proteases cleaving at the carboxyterminal side of Arg and Lys residues and chymotrypsin-like proteases cleaving at the carboxyterminal side of hydrophobic amino acid residues. Proteases of the invention are serine endopeptidases (EC 3.4.21) with acidic pH-optimum (pH optimum<pH 7).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

Endo-protease/Exo-proteases: Polypeptides having protease activity, or proteases, are sometimes also designated peptidases, proteinases, peptide hydrolases, or proteolytic enzymes. Proteases may be of the exo-type (exopeptidases) that hydrolyse peptides starting at either end thereof, or of the endo-type that act internally in polypeptide chains (endo-peptidases).

S53 protease: The term "S53" means a protease activity selected from:
(a) proteases belonging to the EC 3.4.21 enzyme group; and/or
(b) proteases belonging to the EC 3.4.14 enzyme group; and/or
(c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or heterologous (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has protease activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, increased specific activity, increased stability under storage conditions, increased thermostability, and increased expression levels in a recombinant expression host cell.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 199 to 564 of SEQ ID NO: 2. Amino acids 1 to 17 of SEQ ID NO: 2 are a signal peptide, and amino acids 18 to 198 are a propeptide. The N-terminals of the mature S53 polypeptides used according to the present invention were experimentally confirmed based on EDMAN N-terminal sequencing data and Intact MS data. The mature polypeptides are also included as SEQ ID NO: 3 (mature S53 protease 3 from *Meripilus giganteus*. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 595 to 1692 of SEQ ID NO: 1. Nucleotides 1 to 51 of SEQ ID NO: 1 encode a signal peptide, nucleotides 52 to 594 encode a propeptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. In one embodiment the one or more control sequences are heterologous (of different origin/species) to the coding sequence encoding the polypeptide of the invention.

Operably linked: The term "operably linked" means a configuration in which a control sequence is placed at an appropriate position relative to the coding sequence of a polynucleotide such that the control sequence directs expression of the coding sequence.

Parent or parent protease: The term "parent" or "parent protease" means any polypeptide with protease activity to which an alteration is made to produce the enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the −nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the −nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having protease activity. In one aspect, a subsequence contains at least 1098 nucleotides (e.g., nucleotides 595 to 1692 of SEQ ID NO: 1).

Variant: The term "variant" means a polypeptide having protease activity comprising a substitution at one or more (e.g., several) positions. A substitution means replacement of the amino acid occupying a position with a different amino acid. The variants of the present invention have at least 20%, e.g., at least 40%, at least 50%, at least 60%, at least 70%, at least 80%, at least 90%, at least 95%, or at least 100% of the protease activity of the mature polypeptide of SEQ ID NO: 2, disclosed herein as SEQ ID NO: 3.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type protease: The term "wild-type" protease means a protease expressed by a naturally occurring microorganism, such as a bacterium, yeast, or filamentous fungus found in nature.

Conventions for Designation of Variants

For purposes of the present invention, the mature polypeptide comprised in SEQ ID NO: 2 is used to determine the corresponding amino acid residue in another protease. The amino acid sequence of another protease is aligned with the mature polypeptide comprised in SEQ ID NO: 2 (disclosed herein as SEQ ID NO: 3), and based on the alignment, the amino acid position number corresponding to any amino acid residue in the mature polypeptide disclosed as SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease than the *Meripilus giganteus* S53 protease can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G-K-A    |

Multiple alterations. Variants comprising multiple alterations are separated by addition marks ("+"), e.g., "Arg170Tyr+ Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

The present invention relates to protease variants, comprising a substitution at one or more (e.g., several) positions corresponding to specific positions of the mature polypeptide of SEQ ID NO: 2 (a parent protease), wherein the variant has protease activity. As explained herein the specific position numbers may change in case the mature parent protease is different from SEQ ID NO: 3. The improved properties of the variants of the invention falls in the following categories, e.g., increased specific activity, increased stability, e.g., increased storage stability or increased thermostability (measured as increase in half-life after thermal stress (5 minutes a 60° C.) as described in the examples), and increased expression levels in a recombinant expression host cell.

Variants

The present invention provides protease variants, comprising a substitution at one or more positions corresponding to positions 1, 5, 9, 25, 29, 30, 32, 38, 39, 40, 41, 42, 45, 46, 49, 50, 53, 54, 55, 57, 59, 60, 61, 62, 64, 67, 68, 69, 74, 76, 77, 78, 79, 80, 81, 82, 87, 93, 94, 96, 99, 102, 103,105, 109, 111, 112, 114, 115, 117,122, 123, 124, 128,130, 136, 141, 142, 145, 146, 147, 150, 153, 154, 157, 159, 161, 167, 169, 175, 182, 185, 199, 200, 205, 207, 209, 210, 213, 216, 217, 225, 228, 231, 234, 237, 242, 244, 245, 246, 248, 258, 262, 266, 267, 269, 271, 272, 276, 278, 280, 284, 289, 293, 296, 299, 305, 308, 313, 314, 317, 318, 319, 321, 322, 324, 325, 326, 329, 330, 331, 333, 336, 338, 341, 343, 345, 347, 348, 355, 358, 359, 361, 362, 363, and 364 of the polypeptide of SEQ ID NO: 3, and the variant has protease activity. In one embodiment the variants have increased thermo-stability measured as improvement factor, HIF, compared to the protease of SEQ ID NO: 3.

In an embodiment, the variant has sequence identity of at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the mature parent protease.

In another embodiment, the variant has at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one aspect, the number of substitutions in the variants of the present invention is 1-20, e.g., 1-10 and 1-5, such as 1, 2, 3, 4, 5, 6, 7, 8, 9 or 10 substitutions.

In one specific aspect the invention relates to a protease variant, comprising a substitution at one or more positions corresponding to positions 1, 5, 9, 25, 29, 30, 32, 38, 39, 40, 41, 42, 45, 46, 49, 50, 53, 54, 55, 57, 59, 60, 61, 62, 64, 67, 68, 69, 74, 76, 77, 78, 79, 80, 81, 82, 87, 93, 94, 96, 99, 102, 103, 105, 109, 111, 112, 114, 115, 117, 122, 123, 124, 128, 130, 136, 141, 142, 145, 146, 147, 150, 153,154, 157, 159, 161, 167, 169, 175, 182, 185, 199, 200, 205, 207, 209, 210, 213, 216, 217, 225, 228, 231, 234, 237, 242, 244, 245, 246, 248, 258, 262, 266, 267, 269, 271, 272, 276, 278, 280, 284, 289, 293, 296, 299, 305, 308, 313, 314, 317, 318, 319, 321, 322, 324, 325, 326, 329, 330, 331, 333, 336, 338, 341, 343, 345, 347, 348, 355, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased thermo-stability measured as improvement factor, HIF, compared to the protease of SEQ ID NO: 3.

More specifically the variant comprises a substitution at one or more positions selected from the group consisting of: A1T, S5I, S5K, S5L, S5Y, T9H, K25P, S29I, S29P, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, A46E, K49P, S50C, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74H, E74R, D76L, D76R, Q77L, S78D, P79Y, S80L, E81A, E81H, E81K, E81L, E81P, E81Y, A82F, A82L, A82M, A82P, N87S, T93L, T93S, V94S, L96W, G99C, T102L, T102V, T103I, T103K, T103V, I105Q, D109H, D109K, D109M, D109Y, F111H, F111K, F111S, F111Y, Q112R, G114L, N115A, N115C, N115K, N115P, N115R, N115T, N115Y, E117D, E117G, E117H, E117N, E117Q, E117S, I122K, I122R, I123A, N124L, N124V, G128A, G128E, G128F, G128L, G128S, S130D, S130G, S130L, S130N, S130P, L136K, G141T, Q142A, Q142F, Q142L, Q142N, N145V, T146A, T146I, T146L, T146N, I147S, K150F, K150L, K150R, N153A, N153L, N153M, N153P, N153R, N153Y, Q154A, Q154I, Q154L, Q154M, Q154N, Q154T, Q154V, N157I, N157L, Y159H, Q161E, T167F, I169F, I169S, D175I, D175N, Q182C, Q182T, Q182V, H185P, F199L, F199M, M200S, A205S, Q207H, Q207L, V209F, S210T, T213L, T213R, A216R, F217I, F217Y, V225Y, I228L, I228T, I228W, Y231I, S234Q, S237F, S237Q, A242I, A242L, A242V, G244S, S245P, T246S, S248Y, F258P, S262P, V266K, V266R, D267A, D267H, D267L, D267N, Q269L, V271R, S272I, S272K, S272L, S272R, S272T, S272V, S272Y, T276L, T276Y, G278P, D280N, D280S, D280T, D280Y, C284A, C284G, F289Y, I293T, V296A, V296I, R299N, K305S, L308V, P313L, F314I, F314L, S317E, S317N, S317W, S318P, A319F, A319Q, K321L, K321Q, K321S, A322D, L324Q, L324S, N325L, D326P, S329C, S329H, S329I, S329L, S329N, S329T, S329V, S329W, G330Q, S331W, S331Y, P333R, S336K, S336N, N338M, N338Q, N338R, P341S, K343A, K343H, K343S, K343T, K343V, G345S, D347I, P348Y, P355I, P355R, A358L, A358P, A358R, A358Y, K359L, K359S, L361M, T362L, T362N, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.4, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S5K, S5L, S5Y, T9H, K25P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, K49P, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74R, D76L, D76R, Q77L, S78D, P79Y, S80L, E81A, E81H, E81K, E81L, E81P, E81Y, A82M, A82P, N87S, T93L, V94S, G99C, T102L, T102V, T103I, T103K, T103V, I105Q, D109H, D109K, D109M, D109Y, F111H, F111K, F111S, Q112R, G114L, N115C, N115K, N115R, N115T, N115Y, E117D, E117G, E117H, E117N, E117Q, E117S, I122R, N124L, G128F, G128S,S130G, S130N, S130P, L136K, G141T, Q142A, Q142F, Q142L, Q142N, N145V, T146A, T146L, T146N, I147S, K150L, N153M, N153P, N153R, Q154I, Q154L, Q154N, Q154T, Q154V, N157L, Q161E, T167F, I169F, D175N, Q182C, Q182T, Q182V, F199L, F199M, M200S, A205S, Q207H, Q207L, V209F, S210T, T213R, F217I, V225Y, I228L, I228T, I228W, S234Q, S237F, G244S, S245P, T246S, S248Y, F258P, S262P, V266K, V266R, D267A, D267H, D267L, D267N, Q269L, V271R, S272K, S272L, S272R, S272V, S272Y, T276Y, G278P, D280N, D280S, D280T, C284G, F289Y, I293T, V296A, R299N, K305S, L308V, F314L, S317E, S317W, S318P, A319F, A319Q, K321L, K321Q, K321S, A322D, L324Q, L324S, D326P, S329C, S329H, S329I, S329L, S329N, S329W, G330Q, S331W, S331Y, S336K, S336N, P341S, K343A, K343H, K343S, K343T, G345S, D347I, P348Y, P355I, A358L, A358P, A358R, A358Y, K359L, K359S, L361M, T362L, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S5K, S5L, S5Y, T9H, K25P, S30E, F38L, I39G, I39L, I39V, I39Y, D40F, D40G, D40H, D40N, D40P, Q41I, Q41V, F42K, F42Y, K45L, K45M, K45Y, A46C, K49P, S50I, S50L, S50M, S50Q, A53C, A53E, A53V, Q54L, Q54M, F55H, F55L, K57P, K57S, I59G, I59M, I59P, S60P, S61P, S62N, S62P, T64G, T64I, L67V, Q68V, Q68Y, T69C, E74R, D76L, D76R, Q77L, S78D, P79Y, E81A, E81K, E81L, E81P, E81Y, A82P, N87S, T93L, V94S, G99C, T102L, T102V, T103I, T103K, T103V, I105Q, D109H, D109K, D109M, D109Y, F111H, F111K, F111S, Q112R, G114L, N115R, E117G, E117H, E117N, E117Q, E117S, I122R, N124L, G128S, S130G, S130N, S130P, L136K, Q142A, Q142L, Q142N, N145V, T146A, T146L, I147S, K150L, N153M, N153R, Q154I, Q154L, Q154N, Q154T, Q154V, N157L, Q161E, T167F, I169F, D175N, Q182C, Q182V, F199L, F199M, M200S, Q207H, S210T, T213R, F217I, I228L, I228T, I228W, S237F, G244S, T246S, S248Y, F258P, S262P, V266K, V266R, D267A, D267H, D267N, V271R, S272K, S272L, S272R, S272V, S272Y, T276Y, G278P, D280N, D280S, D280T, C284G, F289Y, I293T, V296A, K305S, L308V, F314L, S317E, S317W, S318P, A319F, A319Q, L324S, D326P, S329C, S329I, S329L, S329N, S329W, G330Q, S331W, S331Y, S336N, P341S, K343H, K343S, K343T, G345S, D347I, P355I, A358P, A358R, A358Y, K359L, K359S, T362L, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.8, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S5K, S5Y, K25P, S30E, I39G, I39L, I39Y, D40F, D40G, D40H, D40N, D40P, Q41I, Q41V, F42K, K45M, K45Y, A46C, S50I, S50L, S50M, S50Q, A53C, A53V, Q54M, F55H, F55L, K57P, K57S, I59M, I59P, S60P, S61P, T64I, Q68V, Q68Y, E74R, D76L, D76R, S78D, P79Y, E81A, E81K, E81L, E81P, A82P, N87S, T93L, V94S, T102L, T102V, T103I, T103K, T103V, D109H, D109K, D109M, D109Y, F111H, F111K, F111S, G114L, N115R, E117G, E117H, E117N, I122R, G128S, S130G, S130N, L136K, Q142L, Q142N, N145V, T146A, T146L, I147S, K150L, N153M, N153R, Q154I, Q154L, Q154T, Q154V, N157L, I169F, D175N, F199L, M200S, S210T, T213R, F217I, I228L, I228W, S237F, G244S, T246S, S262P, V266K, D267H, D267N, V271R, S272L, S272V, S272Y, T276Y, G278P, D280S, D280T, C284G, F289Y, I293T, V296A, S317E, S317W, S318P, A319F, L324S, D326P, S329C, S329I, S329W, G330Q, S331Y, S336N, P341S, K343T, D347I, P355I, A358P, A358R, A358Y, K359L, T362L, and A363L, wherein the positions correspond to amino acid positions in the amino acid sequence set forth in SEQ ID NO: 3; and wherein the substitution at the one or more positions provides an increase in thermo-stability measured as improvement factor, HIF, of at least 2.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S5K, I39G, I39L, I39Y, D40H, F42K, K45M, A46C, S50I, S50M, A53C, Q54M, F55H, F55L, K57P, K57S, I59M, I59P, T64I, Q68Y, E74R, D76L, S78D, P79Y, E81K, E81L, N87S, T93L, T102V, T103I, T103K, T103V, D109H, D109Y, F111H, F111K, F111S, N115R, E117G, E117H, I122R, L136K, Q142L, Q142N, T146L, I147S, N153R, Q154L, Q154N, Q154T, N157L, I169F, D175N, F199L, M200S, S210T, T213R, I228L, S237F, T246S, S262P, D267N, V271R, S272V, S272Y, T276Y, D280S, D280T, C284G, F289Y, I293T, V296A, S317E, S317W, A319F, L324S, S329I, S329W, S331Y, S336N, P341S, D347I, P355I, and T362L, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 3.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: I39G, D40H, K45M, A46C, S50I, A53C, F55H, F55L, K57P, T64I, E74R, P79Y, T102V, N115R, E117H, I147S, N157L, D175N, F199L, S210T, I228L, D267N, D280T, C284G, V296A, S317E, A319F, S329I, P341S, D347I, and P355I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 6.4, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In another aspect, the variant comprises or consists of one substitution selected from the group consisting of A1T, S5I, S5K, S5L, S5Y, T9H, K25P, S29I, S29P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, A46E, K49P, S50C, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74H, E74R, D76L, D76R, Q77L, S78D, P79Y, S80L, E81A, E81H, E81K, E81L, E81P, E81Y, A82F, A82L, A82M, A82P, N87S, T93L, T93S, V94S, L96W, G99C, T102L, T102V, T103I, T103K, T103V, I105Q, D109H, D109K, D109M, D109Y, F111H, F111K, F111S, F111Y, Q112R, G114L, N115A, N115C, N115K, N115P, N115R, N115T, N115Y, E117D, E117G, E117H, E117N, E117Q, E117S, I122K, I122R, I123A, N124L, N124V, G128A, G128E, G128F, G128L, G128S, S130D, S130G, S130L, S130N, S130P, L136K, G141T, Q142A, Q142F, Q142L, Q142N, N145V, T146A, T146I, T146L, T146N, I147S, K150F, K150L, K150R, N153A, N153L, N153M, N153P, N153R, N153Y, Q154A, Q154I, Q154L, Q154M, Q154N, Q154T, Q154V, N157I, N157L, Y159H, Q161E, T167F, I169F, I169S, D175I, D175N, Q182C, Q182T, Q182V, H185P, F199L, F199M, M200S, A205S, Q207H, Q207L, V209F, S210T, T213L, T213R, A216R, F217I, F217Y, V225Y, I228L, I228T, I228W, Y231 I, S234Q, S237F, S237Q, A242I, A242L, A242V, G244S, S245P, T246S, S248Y, F258P, S262P, V266K, V266R, D267A, D267H, D267L, D267N, Q269L, V271R, S272I, S272K, S272L, S272R, S272T, S272V, S272Y, T276L, T276Y, G278P, D280N, D280S, D280T, D280Y, C284A, C284G, F289Y, I293T, V296A, V296I, R299N, K305S, L308V, P313L, F314I, F314L, S317E, S317N, S317W, S318P, A319F, A319Q, K321 L, K321Q, K321S, A322D, L324Q, L324S, N325L, D326P, S329C, S329H, S329I, S329L, S329N, S329T, S329V, S329W, G330Q, S331W, S331Y, P333R, S336K, S336N, N338M, N338Q, N338R, P341S, K343A, K343H, K343S, K343T, K343V, G345S, D347I, P348Y, P355I, P355R, A358L, A358P, A358R, A358Y, K359L, K359S, L361M, T362L, T362N, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.4 compared to the parent protease.

The present invention provides protease variants, comprising a substitution at one or more positions corresponding to positions 20, 27, 29, 34, 40, 42, 45, 46, 50, 53, 54, 55, 58, 59, 60, 61, 62, 66, 69, 76, 81, 87, 93, 96, 98, 101, 102, 103, 109, 110, 115, 117, 122, 124, 125, 127, 128, 130, 136, 141, 142, 145, 146, 148, 149, 150, 153, 154, 157, 159, 161, 164, 167,182, 183, 184, 185, 188, 199, 200, 207, 208, 209, 210, 211, 213, 216, 219, 228, 231, 237, 244, 249, 252, 253, 261, 266, 267, 272, 275, 276, 277, 280, 285, 288, 291, 292, 293, 294, 296, 299, 303, 304, 305, 306, 307, 308, 310, 317, 318, 319, 321, 326, 327, 336, 338, 341, 344, 345, 348, 356, 358, 359, 361, 362, 363, and 364 of the polypeptide of SEQ ID NO: 3, and the variant has protease activity. In one embodiment the variants have increased specific activity measured as improvement factor, AIF, compared to the protease of SEQ ID NO: 3.

In an embodiment, the variant has sequence identity of at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the mature parent protease.

In another embodiment, the variant has at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one aspect, the number of substitutions in the variants of the present invention is 1-20, e.g., 1-10 and 1-5, such as 1, 2, 3, 4, 5, 6, 7, 8, 9 or 10 substitutions.

In one specific aspect the invention relates to protease variant, comprising a substitution at one or more positions corresponding to positions 20, 27, 29, 34, 40, 42, 45, 46, 50, 53, 54, 55, 58, 59, 60, 61, 62, 66, 69, 76, 81, 87, 93, 96, 98, 101, 102, 103, 109, 110, 115, 117, 122, 124, 125, 127, 128, 130, 136, 141, 142, 145, 146, 148, 149, 150, 153, 154, 157, 159, 161, 164, 167, 182, 183, 184, 185, 188, 199, 200, 207, 208, 209, 210, 211, 213, 216, 219, 228, 231, 237, 244, 249, 252, 253, 261, 266, 267, 272, 275, 276, 277, 280, 285, 288, 291, 292, 293, 294, 296, 299, 303, 304, 305, 306, 307, 308, 310, 317, 318, 319, 321, 326, 327, 336, 338, 341, 344, 345, 348, 356, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased specific activity measured as improvement factor, AIF, compared to the protease of SEQ ID NO: 3.

More specifically the variant comprises a substitution at one or more positions selected from the group consisting of: G20L, G20R, T27S, S29A, S29C, S29L, S29N, S29P, S29R, A34L, A34N, A34R, D40S, D40Y, F42Y, K45L, K45Y, A46E, A46K, S50A, S50C, S50I, S50L, S50T, A53I, A53K, A53L, A53S, Q54L, F55R, D58M, I59M, I59P, S60C, S60E, S60P, S61D, S61P, S62C, S62N, S66F, S66L, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, I122L, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T146C, T146H, T146I, T146M, T146N, T146Q, T146R, T146V, T146W, S148G, A149V, K150F, N153D, N153F, N153G, N153R, N153Y, Q154C, Q154F, Q154G, Q154I, Q154K, Q154L, Q154M, Q154R, Q154T, Q154V, Q154W, Q154Y, N157A, N157E, N157F, N157M, N157Y, Y159F, YI59G, Y159H, Y159S, Q161A, A164L, T167D, T167V, Q182F, S183A, S183F, S183L, S183M, A184D, A184F, A184H, A184I, A184K, A184L, A184Q, A184R, A184S, A184T, A184V, A184W, A184Y, H185A, H185L, H185P, H185S, N188L, N188Q, F199L, M200F, M200L, Q207F, G208H, G208Y, V209F, V209G, V209H, V209L, V209N, V209W, V209Y, S210E, S210L, S210R, S210T, S210Y, P211F, T213F, T213H, T213I, T213L, T213N, T213R, T213S, T213W, T213Y, A216F, A216L, S219M, I228F, I228H, I228L, I228M, I228Q, I228V, I228Y, Y231F, Y231S, S237F, S237I, S237K, S237L, G244L, G244N, G244P, G244R, G249C, N252F, N252K, N252S, R253C, V261A, V261G, V266C, V266R, D267S, S272I, S272K, S272L, S272M, S272Q, S272R, S272T, S272Y, Q275A, Q275F, Q275K, Q275L, Q275R, Q275V, T276F, T276R, T276V, I277L, I277V, D280F, D280H, D280M, D280N, D280S, D280T, A285S, T288C, T288I, T288V, S291V, V292C, I293M, I293Y, S294T, S294V, V296L, R299P, A303C, A303F, A303H, A303S, A303V, G304H, G304K, G304P, G304R, G304S, G304Y, K305C, K305F, K305H, K305I, K305L, K305M, K305S, K305T, K305Y, S306L, S306M, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, A344P, G345K, G345S, P348G, P348L, P348S, N356L, N356Y, A358F, A358L, A358P, K359C, K359L, K359S, K359W, L361E, L361M, L361P, L361R, L361S, L361T, L361V, T362A, T362C, T362H, T362I, T362K, T362L, T362M, T362P, T362Q, T362R, T362V, T362Y, A363E, A363F, A363L, A363M, A363V, V364F, V364I, V364L, V364M, and V364S, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 1.37, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: G20L, G20R, T27S, S29A, S29C, S29L, S29N, S29P, S29R, A34L, A34N, A34R, F42Y, K45L, K45Y, A46E, A46K, S50A, S50L, A53L, Q54L, F55R, I59M, I59P, S60E, S60P, S61D, S61P, S62N, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T146C, T146H, T146I, T146N, T146Q, T146R, T146V, T146W, S148G, A149V, K150F, N153Y, Q154I, Q154K, Q154L, Q154M, Q154R, Q154W, N157F, N157Y, Y159H, Y159S, Q161A, T167D, Q182F, A184F, A184I, A184K, A184V, A184W, H185A, N188L, F199L, M200F, M200L, Q207F, G208H, G208Y, V209F, V209G, V209H, V209L, V209N, V209W, V209Y, S210E, S210L, S210R, S210T, S210Y, P211F, T213F, T213I, T213L, T213N, T213R, T213S, T213W, A216F, S219M, I228F, I228H, I228L, I228M, I228Q, I228V, I228Y, Y231F, Y231S, S237F, S237I, S237K, S237L, G244N, G249C, N252F, V261A, V261G, V266C, V266R, D267S, S272I, S272L, S272M, S272Q, S272R, S272T, S272Y, Q275F, Q275K, Q275L, Q275R, Q275V, T276F, T276R, T276V, I277L, I277V, D280F, D280H, D280M, D280N, D280S, D280T, A285S, T288C, T288V, I293Y, S294T, S294V, A303F, G304H, G304K, G304P, G304R, G304S, K305C, K305F, K305H, K305I, K305S, K305T, S306L, S306M, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, A344P, G345K, G345S, P348G, P348L, P348S, N356L, N356Y, A358L, K359S, K359W, L361P, L361R, T362C, T362H, T362I, T362K, T362M, T362R, T362Y, A363F, and V364M, wherein the positions correspond to amino acid positions in the amino acid sequence set forth in SEQ ID NO: 3; and wherein the substitution at the one or more positions provides a protease variant having an increase in specific activity measured as improvement factor, AlF, of at least 2.0, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: G20L, G20R, T27S, S29A, S29C, S29L, S29N, S29P, S29R, A34L, A34N, A34R, K45Y, A46E, S50L, A53L, F55R, I59M, S60E, S60P, S61P, S62N, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, E117D, E117F, E117G, E117L, E117N, E117P, E117S, E117W, E117Y, N124I, N124K, N124L, N124M, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145P, N145R, N145S, N145V, N145W, T146A, T146C, T146H, T146I, T146M, T146N, T146Q, T146R, T146V, T146W, S148G, A149V, N153Y, Q154I, Q154L, Q154R, N157F, Y159H, Y159S, T167D, Q182F, A184F, A184I, A184K, A184W, F199L, M200L, G208H, G208Y, V209F, V209G, V209H, V209L, V209N, V209Y, S210E, S210L, T213F, T213I, T213N, T213R, I228F, I228L, I228Q, I228V, I228Y, Y231F, Y231S, S237F, S237I, S237K, S237L, G244N, G249C, V261A, V266R, D267S, S272I, S272L, S272Q, S272R, S272T, S272Y, Q275K, Q275L, Q275R, Q275V, T276F, T276V, I277L, D280F, D280M, D280N, D280S, D280T, A285S, T288V, I293Y, S294T, S294V, G304H, G304K, G304P, G304R, G304S, K305F, K305H, K305I, K305T, S306L, P307C, L308P, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, G345K, G345S, P348G, P348L, P348S, N356L, N356Y, A358L, K359S, L361P, L361R, T362C, T362H, T362I, T362Y, and V364M, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 2.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: G20L, G20R, S29A, S29C, S29N, S29P, A34N, A34R, A46E, S50L, F55R, I59M, S60E, S60P, S61P, S62N, S66M, D76A, D76G, D76K, D76L, D76N, D76P, D76V, D76Y, E81S, N87F, L96F, L96S, L96T, T98L, P101F, P101L, P101M, P101R, T102C, T102I, T103V, D109P, N115A, N115D, N115G, E117D, E117F, E117G, E117L, E117N, E117P, E117W, E117Y, N124I, N124K, N124V, F125L, F125M, L127P, G128N, G128S, G128W, G128Y, S130D, S130F, G141A, G141F, G141L, G141M, G141Q, G141R, Q142A, Q142L, Q142M, Q142S, Q142W, N145G, N145I, N145S, N145W, T146A, T146H, T146N, T146V, T146W, Q154R, Y159H, Y159S, T167D, Q182F, F199L, G208H, G208Y, V209F, V209G, V209H, V209L, V209N, V209Y, S210L, T213I, I228L, I228Q, I228Y, Y231F, Y231S, S237F, S237I, S237K, S237L, G244N, V261A, V266R, D267S, S272L, S272T, S272Y, Q275K, Q275R, T276F, T276V, I277L, D280F, D280N, D280S, D280T, A285S, S294T, G304H, G304K, G304P, G304R, G304S, K305H, K305I, L308P, F310M, F310P, S317C, S317G, S317H, S317I, S317K, S317L, S317R, S317W, S317Y, A319F, K321S, D326P, V327C, S336R, N338H, P341I, P341N, P341R, G345K, G345S, P348G, P348S, N356Y, A358L, L361P, T362I, and V364M, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 2.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S29N, A34N, A34R, I59M, S60P, D76A, D76G, D76K, D76L, D76N, D76P, D76V, D76Y, N87F, L96F, L96S, T98L, P101L, P101M, T102C, T102I, D109P, N115A, E117D, E117F, E117G, E117L, E117N, E117P, E117W, E117Y, N124I, N124K, N124V, F125L, G128N, G128W, S130D, S130F, G141F, G141L, G141M, G141Q, G141R, Q142A, Q142L, Q142M, Q142S, Q142W, N145I, N145S, T146H, T146N, T146W, Q154R, Y159S, T167D, Q182F, V209F, V209H, V209L, I228Q, Y231S, S237I, S237L, D267S, S272T, S272Y, T276F, T276V, D280F, D280S, D280T, A285S, S294T, G304H, G304P, K305H, F310M, F310P, S317C, S317G, S317I, S317K, S317L, S317R, S317W, S317Y, A319F, D326P, V327C, N338H, P341N, P341R, G345K, G345S, P348S, N356Y, and L361P, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 3.0, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: S29N, A34N, A34R, I59M, S60P, D76A, D76K, D76L, D76N, D76P, D76Y, N87F, L96F, D109P, E117F, E117G, E117L, E117N, E117P, E117W, E117Y, N124V, G141F, G141L, G141M, G141R, Q142L, Q142M, Q142S, Q142W, T146H, T146N, Q154R, V209F, V209H, I228Q, T276F, D280T, A285S, S294T, F310M, F310P, S317C, S317I, S317K, S317L, S317R, S317W, D326P, N338H, P341N, P341R, G345K, G345S, P348S, N356Y, and L361P, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 3.8, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: A34N, A34R, D76A, D76K, D76L, D76N, D76Y, N87F, E117F, E117G, E117L, E117N, E117P, E117W, E117Y, G141L, G141M, Q142L, Q142M, Q142S, Q142W, T146H, T146N, Q154R, V209H, T276F, A285S, S294T, F310M, F310P, S317I, S317K, S317R, S317W, N338H, and G345S, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 4.5, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In another aspect, the variant comprises or consists of one substitution selected from the group consisting of: G20L, G20R, T27S, S29A, S29C, S29L, S29N, S29P, S29R, A34L, A34N, A34R, D40S, D40Y, F42Y, K45L, K45Y, A46E, A46K, S50A, S50C, S50I, S50L, S50T, A53I, A53K, A53L, A53S, Q54L, F55R, D58M, I59M, I59P, S60C, S60E, S60P, S61 D, S61P, S62C, S62N, S66F, S66L, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117F, E117F, E117G, E117L, E117N, E117P, E117S, E117W, E117Y, I122L, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T146C, T146H, T146I, T146M, T146N, T146Q, T146R, T146V, T146W, S148G, A149V, K150F, N153D, N153F, N153G, N153R, N153Y, Q154C, Q154F, Q154G, Q154I, Q154K, Q154L, Q154M, Q154R, Q154T, Q154V, Q154W, Q154Y, N157A, N157E, N157F, N157M, N157Y, Y159F, YI59G, Y159H, Y159S, Q161A, A164L, T167D, T167V, Q182F, S183A, S183F, S183L, S183M, A184D, A184F, A184H, A184I, A184K, A184L, A184Q, A184R, A184S, A184T, A184V, A184W, A184Y, H185A, H185L, H185P, H185S, N188L, N188Q, F199L, M200F, M200L, Q207F, G208H, G208Y, V209F, V209G, V209H, V209L, V209N, V209W, V209Y, S210E, S210L, S210R, S210T, S210Y, P211F, T213F, T213H, T213I, T213L, T213N, T213R, T213S, T213W, T213Y, A216F, A216L, S219M, I228F, I228H, I228L, I228M, I228Q, I228V, I228Y, Y231F, Y231S, S237F, S237I, S237K, S237L, G244L, G244N, G244P, G244R, G249C, N252F, N252K, N252S, R253C, V261A, V261G, V266C, V266R, D267S, S272I, S272K, S272L, S272M, S272Q, S272R, S272T, S272Y, Q275A, Q275F, Q275K, Q275L, Q275R, Q275V, T276F, T276R, T276V, I277L, I277V, D280F, D280H, D280M, D280N, D280S, D280T, A285L, A285S, T288C, T288I, T288V, S291V, V292C, I293M, I293Y, S294T, S294V, V296L, R299P, A303C, A303F, A303H, A303S, A303V, G304H, G304K, G304P, G304R, G304S, G304Y, K305C, K305F, K305H, K305I, K305L, K305M, K305S, K305T, K305Y, S306L, S306M, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, A344P, G345K, G345S, P348G, P348L, P348S, N356L, N356Y, A358F, A358L, A358P, K359C, K359L, K359S, K359W, L361E, L361M, L361P, L361R, L361S, L361T, L361V, T362A, T362C, T362H, T362I, T362K, T362L, T362M, T362P, T362Q, T362R, T362V, T362Y, A363E, A363F, A363L, A363M, A363V, V364F, V364I, V364L, V364M, and V364S, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 1.37 compared to the parent protease.

In a further particular embodiment the present invention relates to a protease variant comprising a substitution at one or more positions corresponding to positions 39, 57, 59, 66, 102, 111, 115, 267, 272, 275, or 280 of the polypeptide of SEQ ID NO: 3, and the variant has protease activity, and wherein the variant comprises a substitution selected from the group consisting of: I39L, K57P, I59M, S66T, T102V, F111H, N115K, D267N, S272Y, Q275K, D280S, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Particularly the invention relates to a protease variant comprising a substitution at one or more positions corresponding to positions 39, 57, 59, 66, 102, 111, 115, 267, 272, 275, or 280 of the polypeptide of SEQ ID NO: 3, and the variant has protease activity, and wherein the variant comprises a substitution selected from the group consisting of: I39L, K57P, I59M, S66T, T102V, F111H, N115K, D267N, S272Y, Q275K, D280S, and further wherein the variants have at least 85%, at least 90%, at least 95% identity, at least 96%, at least 97%, at least 98%, or at least 99%, but less than 100%, sequence identity to the amino acid sequence of SEQ ID NO: 3, and wherein the variant has increased thermo-stability measured residual activity after thermal stress for 20 min at 56° C.

In another embodiment the invention relates to a protease variant comprising a substitution at one or more positions corresponding to positions 39, 57, 59, 66, 102, 111, 115, 267, 272, 275, or 280 of the polypeptide of SEQ ID NO: 3, and the variant has protease activity, and wherein the variant comprises a substitution selected from the group consisting of: I39L, K57P, I59M, S66T, T102V, F111H, N115K, D267N, S272Y, Q275K, D280S, and further wherein the variants have at least 85%, at least 90%, at least 95% identity, at least 96%, at least 97%, at least 98%, or at least 99%, but less than 100%, sequence identity to the amino acid sequence of SEQ ID NO: 3, and wherein the variant has increased thermo-stability measured residual activity after thermal stress for 20 min at 56° C., wherein the residual activity is at least 50%, particularly at least 60%, at least 70%, at least 80%.

In another embodiment the invention relates to a protease variant comprising a substitution at one or more positions corresponding to positions 39, 57, 59, 66, 102, 111, 115, 267, 272, 275, or 280 of the polypeptide of SEQ ID NO: 3, and the variant has protease activity, and wherein the variant comprises at least three substitutions selected from the group consisting of: I39L, K57P, I59M, S66T, T102V, F111H, N115K, D267N, S272Y, Q275K, D280S, and further wherein the variants have at least 85%, at least 90%, at least 95% identity, at least 96%, at least 97%, at least 98%, or at least 99%, but less than 100%, sequence identity to the amino acid sequence of SEQ ID NO: 3, and wherein the variant has increased thermo-stability measured residual activity after thermal stress for 20 min at 56° C., wherein the residual activity is at least 50%, particularly at least 60%, at least 70%, at least 80%.

In another embodiment the invention relates to aprotease variant comprising the substitutions corresponding to I39L+S66T+T102V or D267N+S272Y+Q275K+D280S of the polypeptide of SEQ ID NO: 3, and further wherein the variants have at least 85%, at least 90%, at least 95% identity, at least 96%, at least 97%, at least 98%, or at least 99%, but less than 100%, sequence identity to the amino acid sequence of SEQ ID NO: 3, and wherein the variant has increased thermo-stability measured residual activity after thermal stress for 20 min at 56° C., wherein the residual activity is at least 50%, particularly at least 60%, at least 70%, at least 80%.

In another embodiment the invention relates to a protease variant comprising the substitutions corresponding to:
I39L+S66T+T102V;
I39L+S66T+T102V+D267N S272Y+D280S;

I39L+K57P+I59M+S66T+T102V F111H+N115K+ D267N+S272Y,

I39L+K57P+I59M+S66T+T102V+F111H+N115K+ D280S; or

D267N+S272Y+Q275K+D280S in the polypeptide of SEQ ID NO: 3, and further wherein the variants have at least 85%, at least 90%, at least 95% identity, at least 96%, at least 97%, at least 98%, or at least 99%, but less than 100%, sequence identity to the amino acid sequence of SEQ ID NO: 3, and wherein the variant has increased thermostability measured residual activity after thermal stress for 20 min at 56° C., wherein the residual activity is at least 50%, particularly at least 60%, at least 70%, at least 80%.

The present invention provides protease variants, comprising a substitution at one or more positions corresponding to positions 2, 17, 22, 41, 41, 42, 45, 46, 54, 55, 57, 59, 60, 61, 62, 63, 64, 66, 69, 80, 82, 84, 87, 98, 99, 102, 103, 112, 114, 115, 129, 131, 134, 149, 159, 167, 169, 199, 200, 205, 207, 209, 211, 213, 217,242, 250, 266, 267, 269, 270, 271, 272, 274, 278, 279, 280, 284, 288, 291, 292, 294, 296, 301, 307, 314, 329, 331, 333, 336, 362, and 363 of the polypeptide of SEQ ID NO: 3, and the variant has protease activity. In one embodiment the variants have increased expression level measured as improvement factor, EIF, compared to the protease of SEQ ID NO: 3.

In an embodiment, the variant has sequence identity of at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the mature parent protease.

In another embodiment, the variant has at least 80%, at least 85%, at least 90%, at least 91%, at least 92%, at least 93%, at least 94%, at least 95%, such as at least 96%, at least 97%, at least 98%, or at least 99%, but less than 100%, sequence identity to the polypeptide of SEQ ID NO: 3.

In one aspect, the number of substitutions in the variants of the present invention is 1-20, e.g., 1-10 and 1-5, such as 1, 2, 3, 4, 5, 6, 7, 8, 9 or 10 substitutions.

In one specific aspect the invention relates to a protease variant, comprising a substitution at one or more positions corresponding to positions 2, 17, 22, 41, 41, 42, 45, 46, 54, 55, 57, 59, 60, 61, 62, 63, 64, 66, 69, 80, 82, 84, 87, 98, 99, 102, 103, 112, 114, 115, 129,131, 134, 149, 159, 167, 169, 199, 200, 205, 207, 209, 211, 213, 217,242, 250, 266, 267, 269, 270, 271, 272, 274, 278, 279, 280, 284, 288, 291, 292, 294, 296, 301, 307, 314, 329, 331, 333, 336, 362, and 363 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased expression level measured as improvement factor, EIF, compared to the protease of SEQ ID NO: 3.

More specifically the variant comprises a substitution at one or more positions selected from the group consisting of: I2L, A17P, P22V, Q41L, Q41T, Q41V, Q41Y, F42R, K45S, A46L, A46W, Q54R, Q54S, Q54V, Q54Y, F55L, F55N, F55T, F55Y, K57H, K57L, K57V, I59D, I59K, 159R, I59S, I59V, S60I, S60L, S60Q, S60R, S60Y, S61A, S61F, S62H, S62I, S62L, S62R, S62V, T63A, T63E, T63G, T63R, T63V, T64C, T64D, T64M, S66G, T69A, T69F, T69P, T69R, T69Y, S80G, S80L, S80N, S80T, A82H, I84G, N87P, T98C, G99V, T102A, T102H, T103F, T103I, T103V, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, Y159F, Y159L, T167A, T167L, T167S, T167W, I169S, F199Y, M200L, A205S, Q207N, V209P, P211F, P211S, T213S, F217I, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, 1270S, V271F, V271I, V271K, V271M, V271S, V271Y, S272A, S272N, G274R, G278S, V279I, D280Y, C284A, T288A, T288C, T288G, S291V, V292S, S294G, V296P, V296R, V296T, I301T, P307T, F314L, S329D, S329V, S331A, S331G, S331T, P333V, S336G, S336L, S336T, T362R, and A363T, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.38, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: I2L, A17P, P22V, Q41L, Q41Y, F42R, Q54R, Q54S, Q54Y, F55N, F55T, K57L, K57V, I59D, I59S, I59V, S60L, S60Q, S60R, S60Y, S61F, S62L, S62V, T63A, T63E, T63R, T64C, T64D, T64M, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, T167A, T167S, T167W, F199Y, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, 1270S, V271F, V271I, V271K, V271M, S272A, G274R, G278S, T288A, T288C, T288G, V296P, V296R, V296T, F314L, S329D, S329V, S331A, S331G, S331T, P333V, S336G, S336L, and S336T, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: I2L, A17P, P22V, Q41Y, F42R, K57L, I59S, T63A, T63R, Q112H, Q112M, Q112R, Q112S, G114A, G114L, G114P, E129L, E129S, E129Y, N131I, N131S, N131V, Q134L, Q134R, T167W, K250R, V266A, V266L, V266T, D267F, D267L, D267T, D267V, Q269C, Q269F, Q269I, Q269T, Q269V, Q269X, I270A, I270L, 1270S, V271I, V271M, G274R, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.75, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In a further specific embodiment the variant comprises a substitution at one or more positions selected from the group consisting of: Q112M, Q112S, G114L, E129Y, N131 I, Q134R, K250R, D267F, D267L, D267V, Q269C, Q269V, I270A, I270L, V271I, G274R, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.9, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

In another aspect, the variant comprises or consists of one substitution selected from the group consisting of: I2L, A17P, P22V, Q41L, Q41T, Q41V, Q41Y, F42R, K45S, A46L, A46W, Q54R, Q54S, Q54V, Q54Y, F55L, F55N, F55T, F55Y, K57H, K57L, K57V, I59D, I59K, I59R, I59S, I59V, S60I, S60L, S60Q, S60R, S60Y, S61A, S61F, S62H, S62I, S62L, S62R, S62V, T63A, T63E, T63G, T63R, T63V, T64C, T64D, T64M, S66G, T69A, T69F, T69P, T69R, T69Y, S80G, S80L, S80N, S80T, A82H, I84G, N87P, T98C, G99V, T102A, T102H, T103F, T103I, T103V, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, Y159F, Y159L, T167A, T167L, T167S, T167W, I169S, F199Y, M200L, A205S, Q207N, V209P, P211F, P211S, T213S, F217I, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, I270S, V271F, V271I, V271K, V271M, V271S, V271Y, S272A, S272N, G274R, G278S, V279I, D280Y, C284A, T288A, T288C, T288G, S291V, V292S, S294G, V296P, V296R, V296T, I301T, P307T, F314L, S329D, S329V, S331A, S331G, S331T, P333V, S336G, S336L, S336T, T362R, and A363T, wherein the positions correspond to amino acid positions in the amino acid sequence set forth in SEQ ID NO: 3; and wherein the substitution at one or more positions provides a protease variant having an increase in expression level measured as improvement factor, EIF, of at least 1.38 compared to the parent protease.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Therefore even though the protease variants according to the invention may only comprise one specific substitution providing the improved property according to the invention it may still have addition modifications leading to a variant protease having at least 80%, at least 85%, at least 90%, at least 91%, at least 92%, at least 93%, at least 94%, at least 95%, at least 96%, at least 97%, at least 98%, or at least 99%, but less than 100% sequence identity, to the amino acid sequence of the mature parent protease, e.g., the protease of SEQ ID NO: 3. These additional modification should preferably not significantly change the improved properties of the variant protease.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64.

In an embodiment, the variant has improved (increased) specific activity compared to the parent enzyme.

In an embodiment, the variant has improved (increased) stability under storage conditions compared to the parent enzyme.

In an embodiment, the variant has improved (increased) thermostability compared to the parent enzyme.

In an embodiment the variant has improved (increased) expression levels in a recombinant expression host cell.

Parent Proteases

The parent protease may be (a) a polypeptide having at least 80% sequence identity to the mature polypeptide of SEQ ID NO: 2; (b) a polypeptide encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii); or (c) a polypeptide encoded by a polynucleotide having at least 80% sequence identity to the mature polypeptide coding sequence of SEQ ID NO: 1.

In an aspect, the parent has a sequence identity to the mature polypeptide of SEQ ID NO: 2 of at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 3. In another aspect, the parent comprises or consists of amino acids 199 to 564 of SEQ ID NO: 2.

In another aspect, the parent is encoded by a polynucleotide that hybridizes under high stringency conditions, or very high stringency conditions with (i) the mature polypeptide coding sequence of SEQ ID NO: 1, (ii) the cDNA sequence thereof, or (iii) the full-length complement of (i) or (ii) (Sambrook et al., 1989, Molecular Cloning, A Laboratory Manual, 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the cDNA sequence thereof; (iv) the full-length complement thereof; or (v) a subsequence thereof; under high to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 595 to 1692 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the cDNA sequence thereof.

In another embodiment, the parent is encoded by a polynucleotide having a sequence identity to the mature polypeptide coding sequence of SEQ ID NO: 1 of at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

In another aspect, the parent is a *Meripilus giganteus* S53 protease, e.g., the protease of SEQ ID NO: 2 or the mature polypeptide thereof, disclosed herein as SEQ ID NO: 3.

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Nat. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA*

86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus nigerglucoamylase, Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Myceliophthora thermophila* laccase (WO 95/33836), *Rhizomucor miehei* aspartic proteinase.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* niaD, niiA, amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. In a particular embodiment the recombinant host cell comprises the polynucleotide encoding a trehalase polypeptide of the present invention in which the said polynucleotide is heterologous (of different origin/species) to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Nat. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology, Volume* 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a recombinant host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Enzyme Compositions

The present invention also relates to compositions comprising variant protease of the invention. Preferably, the compositions are enriched in such a protease. The term "enriched" indicates that the pullulanase activity of the composition has been increased, e.g., with an enrichment factor of at least 1.1.

The compositions may comprise the variant S53 protease as the major enzymatic component, e.g., a mono-component composition. Alternatively, the compositions may comprise multiple enzymatic activities, such as the variant S53 protease and one or more (e.g., several) enzymes selected from the group consisting of hydrolase, isomerase, ligase, lyase, oxidoreductase, or transferase, e.g., an alpha-galactosidase, alpha-glucosidase, aminopeptidase, alpha-amylase, betaamylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, protease, ribonuclease, transglutaminase, or xylanase. In one embodiment the composition comprises a variant S53 protease of the invention and a carbohydrate-source generating enzyme and optionally an alpha-amylase. In one particular embodiment the composition comprises a variant S53 protease and a glucoamylase. Preferably the enzyme activities comprised in the composition are selected from the variant S53 protease of the invention and one or more enzymes selected from the group consisting of glucoamylase, fungal alpha-amylase.

In an embodiment the glucoamylase comprised in the composition is of fungal origin, preferably from a stain of *Aspergillus*, preferably *A. niger*, *A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, preferable *P. sanguineus*, or a strain of *Gloeophyllum*, such as *G. serpiarium* or *G. trabeum*, or a strain of the *Nigrofomes*.

In an embodiment the glucoamylase is derived from *Trametes*, such as a strain of *Trametes cingulata*, such as the one shown in SEQ ID NO: 4 herein.

In an embodiment the glucoamylase is selected from the group consisting of:
(i) a glucoamylase comprising the polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 4 herein.

In an embodiment the glucoamylase is derived from *Talaromyces*, such as a strain of *Talaromyces emersonii*, such as the one shown in SEQ ID NO: 5 herein.

In an embodiment the glucoamylase is selected from the group consisting of:
(i) a glucoamylase comprising the polypeptide of SEQ ID NO: 5 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576.

In an embodiment the glucoamylase is selected from the group consisting of:
(i) a glucoamylase comprising the polypeptide of SEQ ID NO: 6 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 7 herein.

In an embodiment the glucoamylase is derived from *Gloeophyllum serpiarium*, such as the one shown in SEQ ID NO: 7 herein. In an embodiment the glucoamylase is selected from the group consisting of:
(i) a glucoamylase comprising the polypeptide of SEQ ID NO: 7 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

In another embodiment the glucoamylase is derived from *Gloeophyllum trabeum* such as the one shown in SEQ ID NO: 8 herein. In an embodiment the glucoamylase is selected from the group consisting of:
(i) a glucoamylase comprising the polypeptide of SEQ ID NO: 8 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 8 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

In addition to a glucoamylase the composition may further comprise an alpha-amylase. Particularly the alpha-amylase is an acid fungal alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

Preferably the acid fungal alpha-amylase is derived from the genus *Aspergillus*, especially a strain of *A. terreus, A. niger, A. oryzae, A. awamori*, or *Aspergillus kawachii*, or from the genus *Rhizomucor*, preferably a strain the *Rhizomucor pusillus*, or the genus *Meripilus*, preferably a strain of *Meripilus giganteus*.

In a preferred embodiment the alpha-amylase is derived from a strain of the genus *Rhizomucor*, preferably a strain the *Rhizomucor pusillus*, such as one shown in SEQ ID NO: 3 in WO 2013/006756, such as a Rhizomucorpusillus alpha-amylase hybrid having an *Aspergillus niger* linker and starch-binding domain, such as the one shown in SEQ ID NO: 9 herein, or a variant thereof.

In an embodiment the alpha-amylase is selected from the group consisting of:
(i) an alpha-amylase comprising the polypeptide of SEQ ID NO: 9 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 9 herein.

In a preferred embodiment the alpha-amylase is a variant of the alpha-amylase shown in SEQ ID NO: 9 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 9 for numbering).

In an embodiment the alpha-amylase is derived from a *Rhizomucor pusillus* with an *Aspergillus niger*glucoamylase linker and starch-binding domain (SBD), preferably disclosed as SEQ ID NO: 9 herein, preferably having one or more of the following substitutions: G128D, D143N, preferably G128D+D143N (using SEQ ID NO: 9 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Use of the Variant Proteases of the Invention

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolysate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 4.5 and 5.5. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Alpha-amylases for use in liquefaction are preferably bacterial acid stable alpha-amylases. Particularly the alpha-amylase is from an *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 10 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 10 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations:

I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 10 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 10.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 10 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 10, particularly after position 485, particularly after position 486, particularly after position 487, particularly after position 488, particularly after position 489, particularly after position 490, particularly after position 491, particularly after position 492, more particularly after position 493.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation. Examples of carbohydrate-source generating enzymes are disclosed in the "Enzymes" section below.

In a particular embodiment, the process of the invention further comprises, prior to the conversion of a starch-containing material to sugars/dextrins the steps of:
(x) reducing the particle size of the starch-containing material; and
(y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof). In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Un-Gelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a variant protease of the invention. Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;

wherein step (i) is carried out using at least a glucoamylase, and a variant protease of the invention.

In one embodiment the fermenting organism expresses the variant protease of the invention.

In one embodiment, an alpha amylase is also added in step (i). Steps (i) and (ii) may be performed simultaneously.

The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %., such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase;

(b) saccharifying the liquefied material obtained in step (a) using a carbohydrate-source generating enzyme;

(c) fermenting using a fermenting organism;

wherein a variant protease of the invention is present during step b) or c).

In one embodiment the fermenting organism expresses the variant protease of the invention.

The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C.

In an embodiment fermentation is ongoing for 6 to 120 hours, in particular 24 to 96 hours.

Glucoamylase Present and/or Added in Saccharification and/or Fermentation

The carbohydrate-source generating enzyme present during saccharification may in one embodiment be a glucoamylase. A glucoamylase is present and/or added in saccharification and/or fermentation, preferably simultaneous saccharification and fermentation (SSF), in a process of the invention (i.e., saccharification and fermentation of ungelatinized or gelatinized starch material).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of *Talaromyces*, preferably *T. emersonii* or a strain of *Trametes*, preferably *T. cingulata*, or a strain of *Pycnoporus*, preferably *P. sanguineus*, or a strain of *Gloeophyllum*, such as *G. serpiarium* or *G. trabeum*, or a strain of the *Nigrofomes*.

In an embodiment the glucoamylase is derived from *Trametes*, such as a strain of *Trametes cingulata*, such as the one shown in SEQ ID NO: 4 herein.

In an embodiment the glucoamylase is selected from the group consisting of:
  (i) a glucoamylase comprising the polypeptide of SEQ ID NO: 4 herein;
  (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 4 herein.

In an embodiment the glucoamylase is derived from *Talaromyces*, such as a strain of *Talaromyces emersonii*, such as the one shown in SEQ ID NO: 5 herein.

In an embodiment the glucoamylase is selected from the group consisting of:
  (i) a glucoamylase comprising the polypeptide of SEQ ID NO: 5 herein;
  (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576.

In an embodiment the glucoamylase is selected from the group consisting of:
  (i) a glucoamylase comprising the polypeptide of SEQ ID NO: 6 herein;
  (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 7 herein.

In an embodiment the glucoamylase is derived from *Gloeophyllum serpiarium*, such as the one shown in SEQ ID NO: 7 herein. In an embodiment the glucoamylase is selected from the group consisting of:
  (i) a glucoamylase comprising the polypeptide of SEQ ID NO: 7 herein;
  (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

In another embodiment the glucoamylase is derived from *Gloeophyllum trabeum* such as the one shown in SEQ ID NO: 8 herein. In an embodiment the glucoamylase is selected from the group consisting of:
  (i) a glucoamylase comprising the polypeptide of SEQ ID NO: 8 herein;
  (ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 8 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont.); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in the processes of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 9 herein, or a variant thereof.

In an embodiment the alpha-amylase present and/or added in saccharification and/or fermentation is selected from the group consisting of:
  (i) an alpha-amylase comprising the polypeptide of SEQ ID NO: 9 herein;
  (ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 9 herein.

In a preferred embodiment the alpha-amylase is a variant of the alpha-amylase shown in SEQ ID NO: 9 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 9 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 9 herein, preferably having one or more of the following substitutions: G128D, D143N, preferably G128D+D143N (using SEQ ID NO: 9 for numbering), and wherein the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 9 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an preferred embodiment the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis,* or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of

*Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1 L1 (Appl. Microbiol. Biotech. 77: 61-86), *Thermoanarobacter ethanolicus, Thermoanaerobacter mathranii*, or *Thermoanaerobacter thermosaccharolyticum*. Strains of *Lactobacillus* are also envisioned as are strains of *Corynebacterium glutamicum*R, *Bacillus* thermoglucosidaisus, and *Geobacillus thermoglucosidasius*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

In one embodiment, the fermenting organism is added to the fermentation medium so that the viable fermenting organism, such as yeast, count per mL of fermentation medium is in the range from 105 to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

In an embodiment, the C5 utilizing yeast is a *Saccharomyces cerevisea* strain disclosed in WO 2004/085627.

In an embodiment, the fermenting organism is a C5 eukaryotic microbial cell concerned in WO 2010/074577 (Nedalco).

In an embodiment, the fermenting organism is a transformed C5 eukaryotic cell capable of directly isomerize xylose to xylulose disclosed in US 2008/0014620.

In an embodiment, the fermenting organism is a C5 sugar fermentating cell disclosed in WO 2009/109633.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

The fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid. After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

The invention is further defined in the following numbered paragraphs:

Paragraph 1. A protease variant, comprising a substitution at one or more positions corresponding to positions 1, 5, 9, 25, 29, 30, 32, 38, 39, 40, 41, 42, 45, 46, 49, 50, 53, 54, 55, 57, 59, 60, 61, 62, 64, 67, 68, 69, 74, 76, 77, 78, 79, 80, 81, 82, 87, 93, 94, 96, 99, 102, 103, 105, 109, 111, 112, 114, 115, 117, 122, 123, 124, 128, 130, 136, 141, 142, 145, 146, 147, 150, 153, 154, 157, 159, 161, 167, 169, 175, 182, 185, 199, 200, 205, 207, 209, 210, 213, 216, 217, 225, 228, 231, 234, 237, 242, 244, 245, 246, 248, 258, 262, 266, 267, 269, 271, 272, 276, 278, 280, 284, 289, 293, 296, 299, 305, 308, 313, 314, 317, 318, 319, 321, 322, 324, 325, 326, 329, 330, 331, 333, 336, 338, 341, 343, 345, 347, 348, 355, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased thermo-stability measured as improvement factor, HIF, compared to the protease of SEQ ID NO: 3.

Paragraph 2. The variant of paragraph 1, comprising a substitution at one or more positions selected from the group consisting of: A1T, S5I, S5K, S5L, S5Y, T9H, K25P, S29I, S29P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, A46E, K49P, S50C, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74H, E74R, D76L, D76R, Q77L, S78D, P79Y, S80L, E81A, E81H, E81K, E81L, E81P, E81Y, A82F, A82L, A82M, A82P, N87S, T93L, T93S, V94S, L96W, G99C, T102L, T102V, T103I, T103K, T103V, I105Q, D109H, D109K, D109M, D109Y, F111H, F111K, F111S, F111Y, Q112R, G114L, N115A, N115C, N115K, N115P, N115R, N115T, N115Y, E117D, E117G, E117H, E117N, E117Q, E117S, I122K, I122R, I123A, N124L, N124V, G128A, G128E, G128F, G128L, G128S, S130D, S130G, S130L, S130N, S130P, L136K, G141T, Q142A, Q142F, Q142L, Q142N, N145V, T146A, T146I, T146L, T146N, I147S, K150F, K150L, K150R, N153A, N153L, N153M, N153P, N153R, N153Y, Q154A, Q154I, Q154L, Q154M, Q154N, Q154T, Q154V, N157I, N157L, Y159H, Q161E, T167F, I169F, I169S, D175I, D175N, Q182C, Q182T, Q182V, H185P, F199L, F199M, M200S, A205S, Q207H, Q207L, V209F, S210T, T213L, T213R, A216R, F217I, F217Y, V225Y, I228L, I228T, I228W, Y231I, S234Q, S237F, S237Q, A242I, A242L, A242V, G244S, S245P, T246S, S248Y, F258P, S262P, V266K, V266R, D267A, D267H, D267L, D267N, Q269L, V271R, S272I, S272K, S272L, S272R, S272T, S272V, S272Y, T276L, T276Y, G278P, D280N, D280S, D280T, D280Y, C284A, C284G, F289Y, I293T, V296A, V296I, R299N, K305S, L308V, P313L, F314I, F314L, S317E, S317N, S317W, S318P, A319F, A319Q, K321L, K321Q, K321S, A322D, L324Q, L324S, N325L, D326P, S329C, S329H, S329I, S329L, S329N, S329T, S329V, S329W, G330Q, S331W, S331Y, P333R, S336K, S336N, N338M, N338Q, N338R, P341S, K343A, K343H, K343S, K343T, K343V, G345S, D347I, P348Y, P355I, P355R, A358L, A358P, A358R, A358Y, K359L, K359S, L361M, T362L, T362N, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.4, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 3. The variant of paragraph 1, comprising at least one substitution selected from the group consisting of: S5K, S5L, S5Y, T9H, K25P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, K49P, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74R, D76L, D76R, Q77L, S78D, P79Y, S80L, E81A, E81H, E81K, E81L, E81P, E81Y, A82M, A82P, N87S, T93L, V94S, G99C, T102L, T102V, T103I, T103K, T103V, I105Q, D109H, D109K, D109M, D109Y, F111H, F111K, F111S, Q112R, G114L, N115C, N115K, N115R, N115T, N115Y, E117D, E117G, E117H, E117N, E117Q, E117S, I122R, N124L, G128F, G128S, S130G, S130N, S130P, L136K, G141T, Q142A, Q142F, Q142L, Q142N, N145V, T146A, T146L, T146N, I147S, K150L, N153M, N153P, N153R, Q154I, Q154L, Q154N, Q154T, Q154V, N157L, Q161E, T167F, I169F, D175N, Q182C, Q182T, Q182V, F199L, F199M, M200S, A205S, Q207H, Q207L, V209F, S210T, T213R, F217I, V225Y, I228L, I228T, I228W, S234Q, S237F, G244S, S245P, T246S, S248Y, F258P, S262P, V266K, V266R, D267A, D267H, D267L, D267N, Q269L, V271R, S272K, S272L, S272R, S272V, S272Y, T276Y, G278P, D280N, D280S, D280T, C284G, F289Y, I293T, V296A, R299N, K305S, L308V, F314L, S317E, S317W, S318P, A319F, A319Q, K321L, K321Q, K321S, A322D, L324Q, L324S, D326P, S329C, S329H, S329I, S329L, S329N, S329W, G330Q, S331W, S331Y, S336K, S336N, P341S, K343A, K343H, K343S, K343T, G345S, D347I, P348Y, P355I, A358L, A358P, A358R, A358Y, K359L, K359S, L361M, T362L, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 4. The variant of paragraph 1, comprising at least one substitution selected from the group consisting of: S5K, S5L, S5Y, T9H, K25P, S30E, F38L, I39G, I39L, I39V, I39Y, D40F, D40G, D40H, D40N, D40P, Q41I, Q41V, F42K, F42Y, K45L, K45M, K45Y, A46C, K49P, S50I, S50L, S50M, S50Q, A53C, A53E, A53V, Q54L, Q54M, F55H, F55L, K57P, K57S, I59G, I59M, I59P, S60P, S61P, S62N, S62P, T64G, T64I, L67V, Q68V, Q68Y, T69C, E74R, D76L, D76R, Q77L, S78D, P79Y, E81A, E81K, E81L, E81P, E81Y, A82P, N87S, T93L, V94S, G99C, T102L, T102V, T103I, T103K, T103V, I105Q, D109H, D109K, D109M, D109Y, F111H, F111K, F111S, Q112R, G114L, N115R, E117G, E117H, E117N, E117Q, E117S, I122R, N124L, G128S, S130G, S130N, S130P, L136K, Q142A, Q142L, Q142N, N145V, T146A, T146L, I147S, K150L, N153M, N153R, Q154I, Q154L, Q154N, Q154T, Q154V, N157L, Q161E, T167F, I169F, D175N, Q182C, Q182V, F199L, F199M, M200S, Q207H, S210T, T213R, F217I, I228L, I228T, I228W, S237F, G244S, T246S, S248Y, F258P, S262P, V266K, V266R, D267A, D267H, D267N, V271R, S272K, S272L, S272R, S272V, S272Y, T276Y, G278P, D280N, D280S, D280T, C284G, F289Y, I293T, V296A, K305S, L308V, F314L, S317E, S317W, S318P, A319F, A319Q, L324S, D326P, S329C, S329I, S329L, S329N, S329W, G330Q, S331W, S331Y, S336N, P341S, K343H, K343S, K343T, G345S, D347I, P355I, A358P, A358R, A358Y, K359L, K359S, T362L, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.8, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 5. The variant of paragraph 1, comprising at least one substitution selected from the group consisting of: S5K, S5Y, K25P, S30E, I39G, I39L, I39Y, D40F, D40G, D40H, D40N, D40P, Q41I, Q41V, F42K, K45M, K45Y, A46C, S50I, S50L, S50M, S50Q, A53C, A53V, Q54M, F55H, F55L, K57P, K57S, I59M, I59P, S60P, S61P, T64I, Q68V, Q68Y, E74R, D76L, D76R, S78D, P79Y, E81A, E81K, E81L, E81P, A82P, N87S, T93L, V94S, T102L, T102V, T103I, T103K, T103V, D109H, D109K, D109M, D109Y, F111H, F111K, F111S, G114L, N115R, E117G, E117H, E117N, I122R, G128S, S130G, S130N, L136K, Q142L, Q142N, N145V, T146A, T146L, I147S, K150L, N153M, N153R, Q154L, Q154N, Q154T, Q154V, N157L, I169F, D175N, F199L, M200S, S210T, T213R, F217I, I228L, I228W, S237F, G244S, T246S, S262P, V266K, D267H, D267N, V271R, S272L, S272V, S272Y, T276Y, G278P, D280S, D280T, C284G, F289Y, I293T, V296A, S317E, S317W, S318P, A319F, L324S, D326P, S329C, S329I, S329W, G330Q, S331Y, S336N, P341S, K343T, D347I, P355I, A358P, A358R, A358Y, K359L, T362L, and A363L, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 2.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 6. The variant of paragraph 1, comprising at least one substitution selected from the group consisting of: S5K, I39G, I39L, I39Y, D40H, F42K, K45M, A46C, S50I, S50M, A53C, Q54M, F55H, F55L, K57P, K57S, I59M, I59P, T64I, Q68Y, E74R, D76L, S78D, P79Y, E81K, E81L, N87S, T93L, T102V, T103I, T103K, T103V, D109H, D109Y, F111H, F111K, F111S, N115R, E117G, E117H, I122R, L136K, Q142L, Q142N, T146L, I147S, N153R, Q154L, Q154N, Q154T, N157L, I169F, D175N, F199L, M200S, S210T, T213R, I228L, S237F, T246S, S262P, D267N, V271R, S272V, S272Y, T276Y, D280S, D280T, C284G, F289Y, I293T, V296A, S317E, S317W, A319F, L324S, S329I, S329W, S331Y, S336N, P341S, D347I, P355I, and T362L, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 3.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 7. The variant of paragraph 1, comprising at least one substitution selected from the group consisting of: I39G, D40H, K45M, A46C, S50I, A53C, F55H, F55L, K57P, T64I, E74R, P79Y, T102V, N115R, E117S, I147S, N157L, D175N, F199L, S210T, I228L, D267N, D280T, C284G, V296A, S317E, A319F, S329I, P341S, D347I, and P355I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 6.4, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 8. A protease variant, comprising a substitution at one or more positions corresponding to positions 20, 27, 29, 34, 40, 42, 45, 46, 50, 53, 54, 55, 58, 59, 60, 61, 62, 66, 69, 76, 81, 87, 93, 96, 98, 101, 102, 103, 109, 110, 115, 117, 122, 124, 125, 127, 128, 130, 136, 141, 142, 145, 146, 148, 149, 150, 153, 154, 157, 159, 161, 164, 167, 182, 183, 184, 185, 188, 199, 200, 207, 208, 209, 210, 211, 213, 216, 219, 228, 231, 237, 244, 249, 252, 253, 261, 266, 267, 272, 275, 276, 277, 280, 285, 288, 291, 292, 293, 294, 296, 299, 303, 304, 305, 306, 307, 308, 310, 317, 318, 319, 321, 326, 327, 336, 338, 341, 344, 345, 348, 356, 358, 359, 361, 362, 363, and 364 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased specific activity measured as improvement factor, AIF, compared to the protease of SEQ ID NO: 3.

Paragraph 9. The variant of paragraph 8, comprising at least one substitution selected from the group consisting of: G20L, G20R, T27S, S29A, S29C, S29L, S29N, S29P, S29R, A34L, A34N, A34R, D40S, D40Y, F42Y, K45L, K45Y, A46E, A46K, S50A, S50C, S50I, S50L, S50T, A53I, A53K, A53L, A53S, Q54L, F55R, D58M, I59M, I59P, S60C, S60E, S60P, S61D, S61P, S62C, S62N, S66F, S66L, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, I122L, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142V, N145F, N145G, N145I, N145L, N145P, N145R, N145S, N145V, N145W, T146A, T146C, T146H, T146I, T146M, T146N, T146Q, T146R, T146V, T146W, S148G, A149V, K150F, N153D, N153F, N153G, N153R, N153Y, Q154C, Q154F, Q154G, Q154I, Q154K, Q154L, Q154M, Q154R, Q154T, Q154V, Q154W, Q154Y, N157A, N157E, N157F, N157M, N157Y, Y159F, YI59G, Y159H, Y159S, Q161A, A164L, T167D, T167V, Q182F, S183A, S183F, S183L, S183M, A184D, A184F, A184H, A184I, A184K, A184L, A184Q, A184R, A184S, A184T, A184V, A184W, A184Y, H185A, H185L, H185P, H185S, N188L, N188Q, F199L, M200F, M200L, Q207F, G208H, G208Y, V209F, V209G, V209H, V209L, V209N, V209W, V209Y, S210E, S210L, S210R, S210T, S210Y, P211F, T213F, T213H, T213I, T213L, T213N, T213R, T213S, T213W, T213Y, A216F, A216L, S219M, I228F, I228H, I228L, I228M, I228Q, I228V, I228Y, Y231F, Y231S, S237F, S237I, S237K, S237L, G244L, G244N, G244P, G244R, G249C, N252F, N252K, N252S, R253C, V261A, V261G, V266C, V266R, D267S, S272I, S272K, S272L, S272M, S272Q, S272R, S272T, S272Y, Q275A, Q275F, Q275K, Q275L, Q275R, Q275V, T276F, T276R, T276V, I277L, I277V, D280F, D280H, D280M, D280N, D280S, D280T, A285L, A285S, T288C, T288I, T288V, S291V, V292C, I293M, I293Y, S294T, S294V, V296L, R299P, A303C, A303F, A303H, A303S, A303V, G304H, G304K, G304P, G304R, G304S, G304Y, K305C, K305F, K305H, K305I, K305L, K305M, K305S, K305T, K305Y, S306L, S306M, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, A344P, G345K, G345S, P348G, P348L, P348S, N356L, N356Y, A358F, A358L, A358P, K359C, K359L, K359S, K359W, L361E, L361M, L361P, L361R, L361S, L361T, L361V, T362A, T362C, T362H, T362I, T362K, T362L, T362M, T362P, T362Q, T362R, T362V, T362Y, A363E, A363F, A363L, A363M, A363V, V364F, V364I, V364L, V364M, and V364S, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 1.37, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 10. The variant of paragraph 8, comprising at least one substitution selected from the group consisting of: G20L, G20R, T27S, S29A, S29C, S29L, S29N, S29P, S29R, A34L, A34N, A34R, F42Y, K45L, K45Y, A46E, A46K, S50A, S50L, A53L, Q54L, F55R, I59M, I59P, S60E, S60P, S61D, S61P, S62N, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T146C, T146H, T146I, T146M, T146N, T146Q, T146R, T146V, T146W, T146R, T146V, T146W, S148G, A149V, K150F, N153Y, Q154I, Q154K, Q154L, Q154M, Q154R, Q154W, N157F, N157Y, Y159H, Y159S, Q161A, T167D, Q182F, A184F, A184I, A184K, A184V, A184W, H185A, N188L, F199L, M200F, M200L, Q207F, G208H, G208Y, V209F, V209G, V209H, V209L, V209N, V209W, V209Y, S210E, S210L, S210R, S210T, S210Y, P211F, T213F, T213I, T213L, T213N, T213R, T213S, T213W, A216F, S219M, I228F, I228H, I228L, I228M, I228Q, I228V, I228Y, Y231F, Y231S, S237F, S237I, S237K, S237L, G244N, G249C, N252F, V261A, V261G, V266C, V266R, D267S, S272I, S272L, S272M, S272Q, S272R, S272T, S272Y, Q275F, Q275K, Q275L, Q275R, Q275V, T276F, T276R, T276V, I277L, I277V, D280F, D280H, D280M, D280N, D280S, D280T, A285S, T288C, T288V, I293Y, S294T, S294V, A303F, G304H, G304K, G304P, G304R, G304S, K305C, K305F, K305H, K305I, K305S, K305T, S306L, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, A344P, G345K, G345S, P348G, P348L, P348S, N356L, N356Y, A358L, K359S, K359W, L361P, L361R, T362C, T362H, T362I, T362K, T362M, T362R, T362Y, A363F, and V364M, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 2.0, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 11. The variant of paragraph 8, comprising at least one substitution selected from the group consisting of: G20L, G20R, T27S, S29A, S29C, S29L, S29N, S29P, S29R, A34L, A34N, A34R, K45Y, A46E, S50L, A53L, F55R, I59M, S60E, S60P, S61P, S62N, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, E117D, E117F, E117G, E117L, E117N, E117P, E117S, E117W, E117Y, N124I, N124K, N124L, N124M, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145P, N145R, N145S, N145V, N145W, T146A, T146C, T146H, T146I, T146M, T146N, T146Q, T146R, T146V, T146W, S148G, A149V, N153Y, Q154I, Q154L, Q154R, N157F, Y159H, Y159S, T167D, Q182F, A184F, A184I, A184K, A184W, F199L, M200L, G208H, G208Y, V209F, V209G, V209H, V209L, V209N, V209Y, S210E, S210L, T213F, T213I, T213N, T213R, I228F, I228L, I228Q, I228V, I228Y, Y231F, Y231S, S237F, S237I, S237K, S237L, G244N, G249C, V261A, V266R, D267S, S272I, S272L, S272Q, S272R, S272T, S272Y, Q275K, Q275L, Q275R, Q275V, T276F, T276V, I277L, D280F, D280M, D280N, D280S, D280T, A285S, T288V, I293Y, S294T, S294V, G304H, G304K, G304P, G304R, G304S, K305F, K305H, K305I, K305T, S306L, P307C, L308P, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336R, N338H, N338S, N338T, P341I, P341N, P341R, A344K, A344L, G345K, G345S, P348G, P348L, P348S, N356L, N356Y, A358L, K359S, L361P, L361R, T362C, T362H, T362I, T362Y, and V364M, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 2.2, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 12. The variant of paragraph 8, comprising at least one substitution selected from the group consisting of: G20L, G20R, S29A, S29C, S29N, S29P, A34N, A34R, A46E, S50L, F55R, I59M, S60E, S60P, S61P, S62N, S66M, D76A, D76G, D76K, D76L, D76N, D76P, D76V, D76Y, E81S, N87F, L96F, L96S, L96T, T98L, P101F, P101L, P101M, P101R, T102C, T102I, T103V, D109P, N115A, N115D, N115G, E117D, E117F, E117G, E117L, E117N, E117P, E117Y, N124I, N124K, N124V, F125F, F125M, L127P, G128N, G128S, G128W, G128Y, S130D, S130F, G141A, G141F, G141L, G141M, G141Q, G141R, Q142A, Q142L, Q142M, Q142S, Q142W, N145G, N145I, N145S, N145W, T146A, T146H, T146N, T146V, T146W, Q154R, Y159H, Y159S, T167D, Q182F, F199L, G208H, G208Y, V209F, V209G, V209H, V209L, V209N, V209Y, S210L, T213I, I228L, I228Q, I228Y, Y231F, Y231S, S237F, S237I, S237K, S237L, G244N, V261A, V266R, D267S, S272L, S272T, S272Y, Q275K, Q275R, T276F, T276V, I277L, D280F, D280N, D280S, D280T, A285S, S294T, G304H, G304K, G304P, G304R, G304S, K305H, K305I, L308P, F310M, F310P, S317C, S317G, S317H, S317I, S317K, S317L, S317R, S317W, S317Y, A319F, K321S, D326P, V327C, S336R, N338H, P341I, P341N, P341R, G345K, G345S, P348G, P348S, N356Y, A358L, L361P, T362I, and V364M, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 2.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 13. The variant of paragraph 8, comprising at least one substitution selected from the group consisting of: S29N, A34N, A34R, I59M, S60P, D76A, D76G, D76K, D76L, D76N, D76P, D76V, D76Y, N87F, L96F, L96S, T98L, P101L, P101M, T102C, T102I, D109P, N115A, E117D, E117F, E117G, E117L, E117N, E117P, E117W, E117Y, N124I, N124K, N124V, F125L, G128N, G128W, S130D, S130F, G141F, G141L, G141M, G141Q, G141R, Q142A, Q142L, Q142M, Q142S, Q142W, N145I, N145S, T146H, T146N, T146W, Q154R, Y159S, T167D, Q182F, V209F, V209H, V209L, I228Q, Y231S, S237I, S237L, D267S, S272T, S272Y, T276F, T276V, D280F, D280S, D280T, A285S, S294T, G304H, G304P, K305H, F310M, F310P, S317C, S317G, S317I, S317K, S317L, S317R, S317W, S317Y, A319F, D326P, V327C, N338H, P341N, P341R, G345K, G345S, P348S, N356Y, and L361P, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 3.0, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 14. The variant of paragraph 8, comprising at least one substitution selected from the group consisting of: S29N, A34N, A34R, I59M, S60P, D76A, D76K, D76L, D76N, D76P, D76Y, N87F, L96F, D109P, E117F, E117G, E117L, E117N, E117P, E117W, E117Y, N124V, G141F, G141L, G141M, G141R, Q142L, Q142M, Q142S, Q142W, T146H, T146N, Q154R, V209F, V209H, I228Q, T276F, D280T, A285S, S294T, F310M, F310P, S317C, S317I, S317K, S317L, S317R, S317W, D326P, N338H, P341N, P341R, G345K, G345S, P348S, N356Y, and L361P, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 3.8, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 15. The variant of paragraph 8, comprising at least one substitution selected from the group consisting of: A34N, A34R, D76A, D76K, D76L, D76N, D76Y, N87F, E117F, E117G, E117L, E117N, E117P, E117W, E117Y, G141L, G141M, Q142L, Q142M, Q142S, Q142W, T146H, T146N, Q154R, V209H, T276F, A285S, S294T, F310M, F310P, S317I, S317K, S317R, S317W, N338H, and G345S, wherein the positions correspond to amino acid positions in the amino acid sequence set forth in SEQ ID NO: 3; and wherein the substitution at the one or more positions provides a protease variant having an increase in specific activity measured as improvement factor, AIF, of at least 4.5, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 16. The variant of any of the paragraphs 1-15, wherein the variant comprises a substitution selected from the group consisting of: I39L, K57P, I59M, S66T, T102V, F111H, N115K, D267N, S272Y, Q275K, D280S, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 17. The variant of paragraph 16, wherein the variant has increased thermo-stability measured as residual activity after thermal stress for 20 min at 56° C.

Paragraph 18. The variant of paragraph 17, wherein the residual activity is at least 50%, particularly at least 60%, at least 70%, at least 80%.

Paragraph 19. The variant of any of the paragraphs 16-18, wherein the variant comprises at least three substitutions selected from the group consisting of: I39L, K57P, I59M, S66T, T102V, F111H, N115K, D267N, S272Y, Q275K, D280S.

Paragraph 20. The variant of paragraph 19, comprising the substitutions I39L+S66T+T102V or D267N+S272Y+Q275K+D280S.

Paragraph 21. The variants of any of claim 20, comprising the substitutions:

I39L+S66T+T102V;
I39L+S66T+T102V+D267N S272Y+D280S;
I39L+K57P+I59M+S66T+T102V F111H+N115K+D267N+S272Y;
I39L+K57P+I59M+S66T+T102V+F111H+N115K+D280S; or
D267N+S272Y+Q275K+D280S.

Paragraph 22. A protease variant, comprising a substitution at one or more positions corresponding to positions 2, 17, 22, 41, 41, 42, 45, 46, 54, 55, 57, 59, 60, 61, 62, 63, 64, 66, 69, 80, 82, 84, 87, 98, 99, 102, 103, 112, 114, 115, 129, 131, 134, 149, 159, 167, 169, 199, 200, 205, 207, 209, 211, 213, 217, 242, 250, 266, 267, 269, 270, 271, 272, 274, 278, 279, 280, 284, 288, 291, 292, 294, 296, 301, 307, 314, 329, 331, 333, 336, 362, and 363 of the polypeptide of SEQ ID NO: 3, and the variant has protease activity and wherein the variant has at least 80%, at least 85%, at least 90%, at least 95%, at least 96%, at least 97%, at least 98%, or at least 99%, but less than 100% sequence identity to the mature polypeptide of SEQ ID NO: 3, and wherein the variant has increased expression level measured as improvement factor, EIF, compared to the protease of SEQ ID NO: 3.

Paragraph 23. The variant of paragraph 22, comprising at least one substitution selected from the group consisting of: I2L, A17P, P22V, Q41L, Q41T, Q41V, Q41Y, F42R, K45S, A46L, A46W, Q54R, Q54S, Q54V, Q54Y, F55L, F55N, F55T, F55Y, K57H, K57L, K57V, I59D, I59K, I59R, I59S, I59V, S60I, S60L, S60Q, S60R, S60Y, S61A, S61F, S62H, S62I, S62L, S62R, S62V, T63A, T63E, T63G, T63R, T63V, T64C, T64D, T64M, S66G, T69A, T69F, T69P, T69R, T69Y, S80G, S80L, S80N, S80T, A82H, I84G, N87P, T98C, G99V, T102A, T102H, T103F, T103I, T103V, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, Y159F, Y159L, T167A, T167L, T167S, T167W, I169S, F199Y, M200L, A205S, Q207N, V209P, P211F, P211S, T213S, F217I, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, I270S, V271F, V271I, V271K, V271M, V271S, V271Y, S272A, S272N, G274R, G278S, V279I, D280Y, C284A, T288A, T288C, T288G, S291V, V292S, S294G, V296P, V296R, V296T, I301T, P307T, F314L, S329D, S329V, S331A, S331G, S331T, P333V, S336G, S336L, S336T, T362R, and A363T, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.38, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 24. The variant of paragraph 22, comprising at least one substitution selected from the group consisting of: I2L, A17P, P22V, Q41L, Q41Y, F42R, Q54R, Q54S, Q54Y, F55N, F55T, K57L, K57V, I59D, I59S, I59V, S60L, S60Q, S60R, S60Y, S61F, S62L, S62V, T63A, T63E, T63R, T64C, T64D, T64M, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, T167A, T167S, T167W, F199Y, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, I270S, V271F, V271I, V271K, V271M, S272A, G274R, G278S, T288A, T288C, T288G, V296P, V296R, V296T, F314L, S329D, S329V, S331A, S331G, S331T, P333V, S336G, S336L, and S336T, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.6, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 25. The variant of paragraph 22, comprising at least one substitution selected from the group consisting of: I2L, A17P, P22V, Q41Y, F42R, K57L, I59S, T63A, T63R, Q112H, Q112M, Q112R, Q112S, G114A, G114L, G114P, E129L, E129S, E129Y, N131I, N131S, N131V, Q134L, Q134R, T167W, K250R, V266A, V266L, V266T, D267F, D267L, D267T, D267V, Q269C, Q269F, Q269I, Q269T, Q269V, Q269X, I270A, I270L, I270S, V271I, V271M, G274R, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.75, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 26. The variant of paragraph 22, comprising at least one substitution selected from the group consisting of: Q112M, Q112S, G114L, E129Y, N131I, Q134R, K250R, D267F, D267L, D267V, Q269C, Q269V, I270A, I270L, V271I, G274R, wherein the positions correspond to amino acid positions in the amino acid sequence set forth in SEQ ID NO: 3; and wherein the substitution at the one or more positions provides a protease variant having an increase in expression level measured as improvement factor, EIF, of at least 1.9, and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph 27. The variants of any of paragraphs 1-26, which has at least 85%, at least 90%, at least 91%, at least 92%, at least 93%, at least 94%, at least 95% identity, at least 96%, at least 97%, at least 98%, or at least 99%, but less than 100%, sequence identity to the amino acid sequence of SEQ ID NO: 3.

Paragraph 28. The variant of any of paragraphs 1-26, wherein the number of substitutions is 1-20, e.g., 1-10 and 1-5, such as 1, 2, 3, 4, 5, 6, 7, 8, 9 or 10 substitutions.

Paragraph 29. A polynucleotide encoding the variant of any of paragraphs 1-28.

Paragraph 30. A nucleic acid construct comprising the polynucleotide of paragraph 29.

Paragraph 31. An expression vector comprising the polynucleotide of paragraph 29.

Paragraph 32. A recombinant host cell comprising the polynucleotide of paragraph 29.

Paragraph 33. A method of producing a protease variant, comprising: cultivating the host cell of paragraph 32 under conditions suitable for expression of the variant; and optionally recovering the variant.

Paragraph 34. A composition comprising a variant of any of the paragraphs 1-28.

Paragraph 35. The composition of paragraph 34, further comprising a glucoamylase and optionally a fungal alpha-amylase.

Paragraph 36. A process for producing a fermentation product from starch-containing material comprising simultaneously saccharifying and fermenting starch-containing material using a glucoamylase and a fermenting organism at a temperature below the initial gelatinization temperature of said starch-containing material in the presence of a variant protease of any of the paragraphs 1-28.

Paragraph 37. A process for producing a fermentation product from starch-containing material comprising the steps of:
 (a) liquefying starch-containing material in the presence of an alpha-amylase;
 (b) saccharifying the liquefied material obtained in step (a) using a glucoamylse;
 (c) fermenting using a fermenting organism;
wherein a variant protease of any of the paragraphs 1-28 is present during step b) and/or c).

Paragraph 38. The process of any of the paragraphs 36-37, wherein the fermentation product is ethanol and the fermenting organism is *Saccharomyces cerevisiae*.

Paragraph 39. The process according to any of paragraph 36-38, wherein an alpha-amylase is present or added during saccharification and/or fermentation, particularly an acid fungal alpha-amylase.

Paragraph 40. The process according to paragraph 39, wherein the alpha-amylase is a derived from the genus *Aspergillus*, especially a strain of *A. terreus, A. niger, A. oryzae, A. awamori*, or *Aspergillus kawachii*, or of the genus *Rhizomucor*, preferably a strain the *Rhizomucor pusillus*, or the genus *Meripilus*, preferably a strain of *Meripilus giganteus*.

Paragraph 41. The process of paragraph 40, wherein the alpha-amylase present in saccharification and/or fermentation is derived from a strain of the genus *Rhizomucor*, preferably a strain of *Rhizomucor pusillus*, such as a *Rhizomucor pusillus* alpha-amylase hybrid having an *Aspergillus niger* linker and starch-bonding domain, such as the one shown in SEQ ID NO: 9.

Paragraph 42. The process of paragraph 41, wherein the alpha-amylase present in saccharification and/or fermentation is selected from the group consisting of:
(i) an alpha-amylase comprising the polypeptide of SEQ ID NO: 9;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 9.

Paragraph 43. The process of paragraph 42, wherein the alpha-amylase is derived from a *Rhizomucor pusillus* with an *Aspergillus niger* glucoamylase linker and starch-binding domain (SBD), preferably disclosed as SEQ ID NO: 9, preferably having one or more of the following substitutions: G128D, D143N, preferably G128D+D143N.

Paragraph 44. The process according to any of paragraphs 36-43, wherein the glucoamylase is derived from a strain of *Aspergillus*, preferably *Aspergillus niger* or *Aspergillus awamori*, a strain of *Talaromyces*, especially *Talaromyces emersonii*; or a strain of *Athelia*, especially *Athelia rolfsii*; a strain of *Trametes*, preferably *Trametes cingulata*; a strain of the genus *Gloeophyllum*, e.g., a strain of *Gloeophyllum sepiarium* or *Gloeophyllum trabeum*; a strain of the genus *Pycnoporus*, e.g., a strain of *Pycnoporus sanguineus*; or a mixture thereof.

Paragraph 45. The process of paragraph 44, wherein the glucoamylase is selected from the group consisting of:
(i) a glucoamylase comprising the polypeptide of SEQ ID NO: 4;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 4.

Paragraph 46. The process of paragraph 44, wherein the glucoamylase is selected from the group consisting of:
(i) a glucoamylase comprising the polypeptide of SEQ ID NO: 5;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5.

Paragraph 47. The process of paragraph 44, wherein the glucoamylase is selected from the group consisting of:
(i) a glucoamylase comprising the polypeptide of SEQ ID NO: 6;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6.

Paragraph 48. The process of paragraph 44, wherein the glucoamylase is selected from the group consisting of:
(i) a glucoamylase comprising the polypeptide of SEQ ID NO: 7;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7.

Paragraph 49. The process of paragraph 44, wherein the glucoamylase is selected from the group consisting of:
(i) a glucoamylase comprising the polypeptide of SEQ ID NO: 8;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 8.

Paragraph 50. The process of paragraph 36, wherein the starch-containing material is granular starch.

Paragraph 51. The process of any of paragraphs 37-50, wherein the starch-containing material is derived from corn, wheat, barley, rye, milo, sago, cassava, tapioca, sorghum, rice or potatoes.

Paragraph 52. The host cell of paragraph 32 expressing the variants of any paragraphs 1-28, wherein the host cell is a yeast cell, particularly a *Saccharomyces*, such as *Saccharomyces cerevisiae*.

Paragraph 53. The process of any of the paragraphs 36-37, wherein the host cell of paragraph 52, is applied as the fermenting organism in the fermentation step and the fermentation product is ethanol.

The present invention is further described by the following examples.

EXAMPLES

Example 1: Cloning and Expression of the Wild Type *Meripilus giganteus* Protease III in *Aspergillus oryzae*

Cloning and expression of the *Meripilus giganteus* wild-typeserine protease Ill (MgP3) belonging to family S53 was described in WO 2014/037438. The cloned gene was subsequently transferred as a polymerase chain reaction (PCR) product with suitable overhangs for insertion into P_BGMH0016, disclosed in WO2013/119302 (example 18 and FIG. 10), via USER™ cloning (New England Biolabs, Ipswich, MA, USA) for expression in *Aspergillus oryzae*. Plasmid DNA was used as template in the PCR reaction. The sequence of the forward primer was 5'-AGAGCGAUaccatggtcgccaccagc-3' (SEQ ID NO: 11), and the sequence of the reverse primer was 5'-AACGTCACGUtcacaggccgaccgcggt-3' (SEQ ID NO: 12). Phusion U DNA polymerase (Thermo Fischer Scientific, Grand Island, NY, USA) was used for the PCR reaction.

The PCR reaction consisted of: 10 ng template DNA, 0.5 µM each primer, 1 U Phusion U polymerase, 0.25 mM dNTP, 1× Phusion HF buffer, water to 50 µl. The PCR program consisted of initial denaturation for 30 seconds at 98° C., 35 cycles of amplification (20 seconds at 98° C.; 20 seconds at 60° C.; 2 minutes at 72° C.), and a final extension of 5 minutes at 72° C.

The amplified gene was purified (QAIquick, QIAGEN) and inserted into P_BGMH0016 via USER™ cloning. The reaction contained: 100 ng P_BGMH0016 vector as a PCR product, 500 ng purified PCR product, 1 µl USER™ enzyme, 1 µl Phusion HF buffer, water to 10 µl. The program consisted of 25 minutes at 37° C. and 25 minutes at 25° C. The mixture was transformed into 50 µl chemically competent *Escherichia coli* TOP10 (DH10p) cells, selected for by resistance to ampicillin, and correct clones were verified by sequencing. The plasmid was transformed into protoplasts of *Aspergillus oryzae* Cols1300 disclosed in WO2013/119302, selected for by growth on nitrate as sole nitrogen source, and correct clones were verified by Sanger sequencing. The use of plasmid BGMH0016
takes advantage of the so-called double split-marker system (DSMS) or bi-partite selection marker system (Nielsen et al. 2006, (Efficient PCR-based gene targeting with a recyclable marker for *Aspergillus nidulans*, Fungal Genetics and Biology, 2006(43) 54 to 64)). The double split marker system in pBGMH0016 consists of the two split markers in the *Aspergillus oryzae* COLS1300 strain: niaDΔ and niiAΔ, which flank the amdS selection marker. Only the correct insertion of the donor DNA via double homologous recombination in the partial niaD and niiA genes, respectively, in host cell COLS1300 will restore the functionality of both genes and both genes are required for the cell to grow on a medium containing sodium nitrate as sole nitrogen source. This also ensures a targeted insertion in place of the amdS gene in single copy.

Each of the specific variants of the MgP3 according to the invention may be cloned and expressed as disclosed above.

Example 2: Stability Assay for Specific Variants According to the Invention

The stability of substitution variants of MgP3 relative to MgP3 having the amino acid sequence of SEQ ID NO: 3 is determined by incubating the protease samples under defined conditions ("stress conditions") in a buffered solution. The temperature and duration of the incubation is chosen such that the remaining activity of the wild-type after the incubation is equal to approximately 20% of the activity of a similar sample incubated under defined conditions ("reference conditions") that do not lead to loss of activity when incubated for the same duration. The activity after incubation under stress conditions or reference conditions is determined using the Suc-AAPF-pNA assay described below.

A. Protease Activity Determination Using the Suc-AAPF-pNA Assay

In order to determine the protease activity of the MgP3 protease and variants hereof, the hydrolysis of N-succinyl-L-alanyl-L-alanyl-L-propyl-L-phenyl-p-nitroanilide (Suc-AAPF-pNA) was measured.

The reagent solutions used are:

Dilution Buffer: 100 mM Succinic acid, 1 mM $CaCl_2$, 150 mM KCl, 0.01% Triton X-100, pH 4.5. Assay Buffer: Dilution buffer with 1 mM Suc-AAPF-pNA (N-succinyl-L-alanyl-L-alanyl-L-propyl-L-phenyl-p-nitroanilide, Bachem 4002299.1000), 12.5 µL mL$^{-1}$ DMSO (Amresco 0231).

MgP3 variants were grown in 96-well microtiter plates to produce culture supernatant. On each plate, four wells contained culture supernatant with wild-type MgP3 (SEQ ID NO: 3).

The Suc-AAPF-pNA assay is performed in disposable polystyrene flat-bottom 384-well micro plates (Perkin-Elmer 6007649). First, protease samples (culture supernatant) are diluted 5-fold in Dilution Buffer. Subsequently, 25 µL of the diluted protease sample is added to each well of the 384-well micro assay plate, followed by addition of 25 µL Assay Buffer. The solutions are mixed thoroughly and the absorbance was recorded at 405 nm for 5 minutes, and the initial rate was calculated per well from the maximum velocity of a window of 270 seconds.

B. Stability Assay

The stability of the MgP3 variants in buffer is determined by determining the Stability Half-life of the protease variants as the negative value of the stress time in hours divided by the logarithm to base 2 of the ratio of the protease activity of the variants under destabilizing conditions ("stress conditions") to the protease activity of the same variants under non-destabilizing conditions ("reference conditions"). The kinetic slopes were subjected to quality control and variant samples that either 1) displayed a $R^2$ of linear fit that was below the 25% quartile of the $R^2$ fit of the wild type control in a) stressed condition or b) non-stressed condition, or 2) displayed a Vmax below the 75% quartile of Vmax of the non-expressing controls, in the a) stressed condition or b) non-stressed condition, were removed. The ratio of the initial rate of the stressed and non-stressed supernatants originating from the same clone were defined as $$\text{Ratio} = \frac{Vmax \text{ Stressed}}{Vmax \text{ Unstressed}}.$$

The samples that displayed a ratio above the 90% quantile of the wild type control were counted as hits, and were picked and regrown and sequenced. The half-life at 60° C.

$$\left( t_{60° C.}^{1/2} \right)$$

was calculated based on the $$\frac{Ln(0.5)}{\left( \frac{Ln(\text{Ratio})}{5} \right)}$$

equation, where Half-life is provided in minutes.

The reagent solutions used are:
Dilution Buffer: As described in A.
Assay Buffer: As described in A.

The assay is performed in disposable polystyrene 96-well PCR plates (e.g. Thermo Scientific AB-0601), except for the Suc-AAPF-pNA assay described in A, which is performed in 384-well micro plates.

First, 25 µl the culture supernatants containing the protease is transferred to two fresh plates: one termed "Stress Plate" and one termed "Reference Plate". The Stress Plate is fitted with a lid and incubated in a thermocycler for 5 minutes at 60° C. The Reference Plate is fitted with a lid and incubated at 21° C. (ambient temperature) meanwhile. After incubation the culture supernatants of the Stress Plate and the Reference Plate are transferred to 384-well plates and 25 µL Assay Buffer is added to each well on both the Stress Plate and the Reference Plate, and they are mixed thoroughly.

Half-Life Improvement Factor (HIF)

The half-life improvement factor (HIF) correlates the Stability Half-life of a variant protease with that of the reference protease. Calculation of the improvement factor based on Stability Half-life (SH) was done according to the following equation: HIF=(SH of the variant)/(SH of MgP3 (SEQ ID NO: 3)).

A half-life improvement factor that is greater than 1 (HIF>1) indicates an improved stability of a variant as compared to the reference, while a HIF of 1 (HIF=1) identifies a variant which is on par with the reference, and a HIF of less than 1 (HIF<1) identifies a variant that is less stable the reference. The HIF of all mutations with improved stability is shown in the table 1 below. If a given substitution was observed more than once, the median HIF of all observations is shown.

TABLE 1

| Substitution using SEQ ID NO: 3 for numbering | HIF |
| --- | --- |
| S317N | 1.40 |
| Y231I | 1.41 |
| N325L | 1.41 |
| N153Y | 1.41 |
| I169S | 1.41 |
| S130D | 1.41 |
| T276L | 1.42 |
| G128A | 1.42 |
| N157I | 1.42 |
| T213L | 1.42 |
| K150F | 1.43 |
| T362N | 1.44 |
| G128E | 1.44 |
| N153L | 1.44 |
| A242I | 1.44 |
| P313L | 1.44 |
| D280Y | 1.45 |
| S130L | 1.45 |
| V296I | 1.45 |
| F314I | 1.45 |
| A242V | 1.45 |
| Q154M | 1.45 |
| F217Y | 1.46 |
| K150R | 1.46 |
| N153A | 1.46 |
| S29P | 1.46 |
| C284A | 1.47 |
| H185P | 1.48 |
| A242L | 1.48 |
| N338Q | 1.48 |
| F111Y | 1.49 |
| N338R | 1.49 |
| Y159H | 1.49 |
| P333R | 1.50 |
| K343V | 1.50 |
| A82F | 1.51 |
| Q154A | 1.52 |
| S329T | 1.53 |
| T93S | 1.53 |
| L96W | 1.54 |
| I123A | 1.55 |
| N338M | 1.55 |
| S272T | 1.55 |
| A216R | 1.55 |
| N124V | 1.55 |
| S272I | 1.55 |
| A46E | 1.55 |
| S5I | 1.56 |
| S237Q | 1.56 |
| P355R | 1.56 |
| I122K | 1.56 |
| S50C | 1.56 |
| S329V | 1.56 |
| E74H | 1.57 |
| D175I | 1.57 |
| N115A | 1.58 |
| S29I | 1.58 |

TABLE 1-continued

| Substitution using SEQ ID NO: 3 for numbering | HIF |
| --- | --- |
| G128L | 1.58 |
| N115P | 1.59 |
| A1T | 1.59 |
| T146I | 1.59 |
| A82L | 1.60 |
| S61L | 1.60 |
| Q269L | 1.60 |
| S62C | 1.60 |
| E117D | 1.60 |
| S329H | 1.60 |
| N115T | 1.61 |
| A363G | 1.62 |
| K321S | 1.62 |
| Q54V | 1.63 |
| A205S | 1.63 |
| Q182T | 1.63 |
| S80L | 1.65 |
| L324Q | 1.65 |
| N115C | 1.65 |
| V225Y | 1.65 |
| N115K | 1.65 |
| V209F | 1.66 |
| N115Y | 1.66 |
| K343A | 1.66 |
| A358L | 1.66 |
| N153P | 1.67 |
| A82M | 1.68 |
| G141T | 1.69 |
| F42S | 1.69 |
| F42C | 1.69 |
| S234Q | 1.69 |
| Q142F | 1.70 |
| P348Y | 1.70 |
| K32W | 1.71 |
| E81H | 1.72 |
| S336K | 1.72 |
| A322D | 1.74 |
| R299N | 1.74 |
| D267L | 1.74 |
| L361M | 1.74 |
| T146N | 1.75 |
| K321Q | 1.75 |
| K321L | 1.76 |
| G128F | 1.76 |
| S29R | 1.77 |
| Q207L | 1.79 |
| Q54I | 1.80 |
| S245P | 1.80 |
| K45L | 1.80 |
| Q154I | 1.81 |
| S130P | 1.81 |
| G99C | 1.81 |
| Q54L | 1.82 |
| Q77L | 1.82 |
| T69C | 1.83 |
| F42Y | 1.84 |
| F258P | 1.85 |
| S62N | 1.85 |
| S272R | 1.87 |
| E117Q | 1.87 |
| A319Q | 1.87 |
| Q161E | 1.87 |
| T9H | 1.87 |
| E117S | 1.90 |
| S329L | 1.90 |
| S272K | 1.90 |
| G345S | 1.90 |
| I105Q | 1.91 |
| S248Y | 1.91 |
| K359S | 1.91 |
| L67V | 1.93 |
| S62P | 1.93 |
| Q142A | 1.93 |
| D267A | 1.94 |
| I228T | 1.97 |
| F314L | 1.98 |
| T167F | 1.99 |
| S5L | 1.99 |

TABLE 1-continued

| Substitution using SEQ ID NO: 3 for numbering | HIF |
|---|---|
| I39V | 2.02 |
| Q182V | 2.02 |
| V364I | 2.03 |
| D280N | 2.04 |
| K305S | 2.05 |
| I59G | 2.05 |
| N124L | 2.07 |
| S331W | 2.08 |
| K49P | 2.08 |
| Q112R | 2.09 |
| K343S | 2.09 |
| T64G | 2.10 |
| S329N | 2.11 |
| Q207H | 2.11 |
| V266R | 2.12 |
| A53E | 2.12 |
| L308V | 2.12 |
| E81Y | 2.14 |
| F199M | 2.15 |
| K343H | 2.15 |
| Q182C | 2.17 |
| F38L | 2.18 |
| Q154V | 2.25 |
| D40P | 2.25 |
| E81P | 2.27 |
| E81A | 2.27 |
| A358Y | 2.28 |
| D76R | 2.28 |
| N153M | 2.28 |
| K45Y | 2.32 |
| E117N | 2.32 |
| S130G | 2.32 |
| I228W | 2.33 |
| S60P | 2.34 |
| A53V | 2.35 |
| D326P | 2.36 |
| K25P | 2.36 |
| D40G | 2.41 |
| S61P | 2.43 |
| S50L | 2.43 |
| D40N | 2.44 |
| A363L | 2.44 |
| A358P | 2.48 |
| G114L | 2.51 |
| A358R | 2.52 |
| T102L | 2.54 |
| V266K | 2.56 |
| D40F | 2.60 |
| G128S | 2.61 |
| G278P | 2.63 |
| S30E | 2.63 |
| S272L | 2.66 |
| S130N | 2.72 |
| V94S | 2.72 |
| T146A | 2.73 |
| S5Y | 2.74 |
| S318P | 2.77 |
| S50Q | 2.80 |
| Q41I | 2.81 |
| K359L | 2.82 |
| S329C | 2.83 |
| D109K | 2.87 |
| G244S | 2.87 |
| G330Q | 2.88 |
| F217I | 2.90 |
| D109M | 2.95 |
| Q41V | 2.97 |
| Q68V | 3.00 |
| D267H | 3.05 |
| K343T | 3.10 |
| A82P | 3.10 |
| N145V | 3.11 |
| K150L | 3.12 |
| V271R | 3.22 |
| Q142L | 3.22 |
| Q154T | 3.25 |
| T276Y | 3.28 |
| T213R | 3.32 |
| Q154L | 3.32 |
| T103K | 3.41 |
| S5K | 3.46 |
| S78D | 3.48 |
| T146L | 3.61 |
| D280S | 3.65 |
| F111S | 3.65 |
| Q54M | 3.66 |
| D109Y | 3.67 |
| I59P | 3.68 |
| E81K | 3.68 |
| N153R | 3.68 |
| I59M | 3.69 |
| F289Y | 3.70 |
| I39L | 3.72 |
| F111H | 3.73 |
| E81L | 3.75 |
| D76L | 3.77 |
| F111K | 3.80 |
| L324S | 3.88 |
| N87S | 3.90 |
| S237F | 3.93 |
| Q154N | 3.93 |
| S336N | 4.03 |
| S331Y | 4.20 |
| D109H | 4.21 |
| S50M | 4.30 |
| S329W | 4.33 |
| K57S | 4.38 |
| S262P | 4.44 |
| M200S | 4.44 |
| F42K | 4.72 |
| I39Y | 4.72 |
| T362L | 4.75 |
| Q142N | 4.75 |
| S317W | 4.80 |
| I293T | 4.83 |
| S272V | 4.91 |
| T93L | 5.05 |
| S272Y | 5.08 |
| Q68Y | 5.26 |
| E117G | 5.36 |
| T103I | 5.58 |
| T103V | 5.68 |
| L136K | 6.20 |
| T246S | 6.25 |
| I122R | 6.30 |
| I169F | 6.38 |
| K57P | 6.42 |
| K45M | 6.49 |
| F199L | 6.73 |
| D280T | 7.21 |
| D347I | 7.51 |
| C284G | 7.52 |
| I39G | 7.85 |
| T102V | 8.00 |
| D267N | 8.09 |
| T64I | 8.21 |
| A46C | 8.47 |
| S329I | 8.67 |
| D40H | 9.75 |
| D175N | 10.69 |
| I147S | 10.74 |
| F55L | 10.81 |
| F55H | 11.30 |
| S50I | 13.04 |
| I228L | 13.38 |
| P341S | 13.77 |
| E117H | 14.46 |
| E74R | 15.02 |
| S210T | 15.59 |
| N157L | 19.44 |
| P355I | 21.59 |
| N115R | 21.69 |
| A53C | 29.73 |

TABLE 1-continued

| Substitution using SEQ ID NO: 3 for numbering | HIF |
|---|---|
| A319F | 32.88 |
| V296A | 46.40 |
| P79Y | 69.73 |
| S317E | 267.32 |

Example 3: Specific Activity Assay for Specific Variants According to the Invention The specific activity of substitution variants of MgP3 relative to MgP3 having the amino acid sequence of SEQ ID NO: 3 is determined by comparing the total activity of the protease samples to the amount of protein in the sample. The activity in the culture supernatants are determined using the Suc-AAPF-pNA assay and protein concentration was determined by enzyme-linked immunosorbent assay (ELISA), both described below.

A. Protease Activity Determination Using the Suc-AAPF-pNA Assay

In order to determine the protease activity of the MgP3 protease and variants hereof, the hydrolysis of N-succinyl-L-alanyl-L-alanyl-L-propyl-L-phenyl-p-nitroanilide (Suc-AAPF-pNA) was measured.

The reagent solutions used are:

Dilution Buffer: 100 mM Succinic acid, 1 mM CaCl$_2$, 150 mM KCl, 0.01% Triton X-100, pH 4.5.

Assay Buffer: Dilution buffer with 1 mM Suc-AAPF-pNA (N-succinyl-L-alanyl-L-alanyl-L-propyl-L-phenyl-p-nitroanilide, Bachem 4002299.1000), 12.5 µL mL$^{-1}$ DMSO (Amresco 0231).

MgP3 variants were grown in 96-well microtiter plates to produce culture supernatant. On each plate, four wells contained culture supernatant with wild-type MgP3 (SEQ ID NO: 3).

The Suc-AAPF-pNA assay is performed in disposable polystyrene flat-bottom 384-well micro plates (Perkin-Elmer 6007649). First, protease samples (culture supernatant) are diluted 5-fold in Dilution Buffer. Subsequently, 25 µL of the diluted protease sample is added to each well of the 384-well micro assay plate, followed by addition of 25 µL Assay Buffer. The solutions are mixed thoroughly and the absorbance was recorded at 405 nm for 5 minutes, and the initial rate was calculated per well from the maximum velocity of a window of 270 seconds.

B. Protein Quantification by Enzyme-Linked Immunosorbent Assay (ELISA)

The reagent solutions used are:

TBS-T: 20 mM Tris, 150 mM NaCl, 0.1% Tween-20, pH 7.5.

PBS buffer: 137 mM NaCl, 2.7 mM KCl, 10 mM Na$_2$HPO$_4$ 1.8 mM KH$_2$PO$_4$.

TMB plus 2 (KemEnTech diagnostics A/S) is pre-made and ready for use.

The protease sample (culture supernatant) was diluted 2000-fold in TBS-T and analyzed by ELISA, using a rabbit-raised HRP-conjugated MgP3-antibody. ELISA quantification is carried out in blocked 384 microtiter plate (Nunc MaxiSorp) coated with "protein A"-purified rabbit Polyclonal-anti-MgP3 antibodies. The diluted enzyme samples (as well as standards and controls) are transferred to the antibody-plate, incubated, and followed by repeated vigorous washing with PBS buffer. Detection is carried out using the same polyclonal antibodies, however in a HRP-labeled form (LL-HRP conjugation). Anti-MgP3:HRP conjugate in TBS-T in appropriate dilution is added, followed by PBS washing. Signal read as end-point OD-(620 nM) subsequent to TMB plus 2 substrate addition.

Concentrations were calculated from using a non-linear function that were derived from the MgP3-containing standard samples that were located on external plates, as well as MgP3 standard wells that were added to each plate in the screening flow.

C. Protease Specific Activity Calculation for Variants

A linear fit was calculated per plate based on the initial rate and standard concentrations of the standard samples. Plates were removed that were outside of the 2.5-97.5% quantile range for the fit parameters slope and intercept. A concentration prediction was derived from the Vmax by entering it into the inverted linear fit of the standards (per plate). Specific activity was calculated as $$\text{Specific activity} = \frac{\text{Concentration (Predicted)}}{\text{Concentration (ELISA)}}.$$

For the hit selection the samples that displayed <30 µg mL$^{-1}$, ELISA concentration were only considered. The samples that displayed a specific activity above the 95% quantile of the wild type control were counted as hits, and were sequenced.

Improvement Factor for Specific Activity (AIF)

The improvement factor for specific activity (AIF) correlates the specific activity of a variant protease with that of the reference protease. Calculation of the improvement factor based on specific activity (SA) was done according to the following equation: AIF=(SA of the variant)/(SA of MgP3 (SEQ ID NO: 3)).

A specific activity improvement factor that is greater than 1 (AIF>1) indicates an improved specific activity of a variant as compared to the reference, while an AIF of 1 (AIF=1) identifies a variant which is on par with the reference, and an AIF of less than 1 (AIF<1) identifies a variant with lower specific activity than the reference. The AIF of all mutations with improved specific activity is shown in the table 2 below. If a given substitution was observed more than once, the median AIF of all observations is shown.

TABLE 2

| Substitution using SEQ ID NO: 3 for numbering | AIF |
|---|---|
| S183F | 1.38 |
| S183L | 1.38 |
| H185L | 1.41 |
| N188Q | 1.44 |
| S183M | 1.52 |
| T362A | 1.60 |
| T362V | 1.62 |
| Y159F | 1.62 |
| H185S | 1.62 |
| A184H | 1.63 |
| Q154C | 1.63 |
| N153G | 1.64 |
| L361S | 1.64 |
| S183A | 1.65 |
| A358F | 1.65 |
| V364S | 1.65 |
| N153R | 1.65 |
| A184Q | 1.66 |
| Q154Y | 1.66 |
| N157M | 1.67 |
| N153F | 1.68 |
| L361V | 1.68 |

TABLE 2-continued

| Substitution using SEQ ID NO: 3 for numbering | AIF |
|---|---|
| Q154T | 1.69 |
| V364F | 1.69 |
| L361M | 1.71 |
| T362Q | 1.72 |
| Y159G | 1.72 |
| A363L | 1.72 |
| A363E | 1.73 |
| L361E | 1.73 |
| Q275A | 1.74 |
| S60C | 1.74 |
| S50T | 1.76 |
| A285L | 1.76 |
| A184T | 1.77 |
| A363V | 1.78 |
| G244L | 1.78 |
| V364L | 1.78 |
| A184D | 1.78 |
| N252S | 1.78 |
| H185P | 1.78 |
| V364I | 1.79 |
| Q154F | 1.79 |
| A184Y | 1.82 |
| T362P | 1.83 |
| N252K | 1.84 |
| A164L | 1.84 |
| Q154G | 1.84 |
| S50C | 1.85 |
| S50I | 1.85 |
| A53K | 1.85 |
| K359L | 1.86 |
| N157E | 1.86 |
| A53I | 1.86 |
| K305M | 1.87 |
| N157A | 1.87 |
| S66L | 1.87 |
| N153D | 1.88 |
| A184L | 1.88 |
| S291V | 1.88 |
| A358P | 1.88 |
| A303H | 1.88 |
| D58M | 1.89 |
| K305Y | 1.89 |
| D40S | 1.90 |
| V296L | 1.90 |
| V292C | 1.90 |
| I293M | 1.90 |
| A363M | 1.91 |
| K359C | 1.91 |
| A53S | 1.92 |
| G304Y | 1.92 |
| T288I | 1.93 |
| A303S | 1.94 |
| T362L | 1.94 |
| A184S | 1.94 |
| T213H | 1.94 |
| S272K | 1.94 |
| K305L | 1.95 |
| R253C | 1.95 |
| I122L | 1.95 |
| S66F | 1.95 |
| A216L | 1.95 |
| A184R | 1.95 |
| Q154V | 1.96 |
| A303V | 1.97 |
| A303C | 1.97 |
| G244R | 1.97 |
| T167V | 1.97 |
| L361T | 1.99 |
| S62C | 1.99 |
| T213Y | 1.99 |
| G244P | 1.99 |
| S306M | 1.99 |
| R299P | 2.00 |
| D40Y | 2.00 |
| A216F | 2.00 |
| S272M | 2.00 |
| Q54L | 2.01 |
| I277V | 2.01 |
| K150F | 2.02 |
| N115P | 2.03 |
| Q154W | 2.03 |
| N124D | 2.03 |
| L308T | 2.04 |
| A184V | 2.04 |
| S210R | 2.04 |
| K45L | 2.04 |
| Q207F | 2.04 |
| T362M | 2.04 |
| N252F | 2.05 |
| M200F | 2.05 |
| S210Y | 2.05 |
| S306R | 2.05 |
| V209W | 2.06 |
| A303F | 2.06 |
| V266C | 2.06 |
| I228H | 2.06 |
| Q161A | 2.07 |
| A363F | 2.07 |
| T276R | 2.08 |
| T362K | 2.08 |
| Q154K | 2.09 |
| T213S | 2.09 |
| A46K | 2.09 |
| N124T | 2.11 |
| Q154M | 2.11 |
| I59P | 2.11 |
| N145L | 2.12 |
| N157Y | 2.12 |
| F42Y | 2.12 |
| Q275F | 2.12 |
| H185A | 2.12 |
| T213L | 2.13 |
| T288C | 2.13 |
| V261G | 2.14 |
| S219M | 2.15 |
| I228M | 2.15 |
| K359W | 2.15 |
| K305S | 2.16 |
| S50A | 2.16 |
| S61D | 2.16 |
| N188L | 2.17 |
| P211F | 2.17 |
| K305C | 2.18 |
| S210T | 2.18 |
| T213W | 2.18 |
| A344P | 2.19 |
| D280H | 2.19 |
| T362R | 2.20 |
| Q154I | 2.22 |
| N157F | 2.22 |
| K359S | 2.23 |
| T213F | 2.23 |
| K321R | 2.23 |
| S148G | 2.24 |
| F310Y | 2.24 |
| L361R | 2.24 |
| V327T | 2.24 |
| Q275L | 2.25 |
| S272Q | 2.26 |
| P348L | 2.26 |
| L127C | 2.26 |
| P307C | 2.27 |
| I293Y | 2.27 |
| S210E | 2.27 |
| Q275V | 2.27 |
| A184K | 2.28 |
| N145P | 2.28 |
| A149V | 2.29 |
| T213N | 2.29 |
| N124M | 2.29 |
| T146Q | 2.29 |
| S294V | 2.30 |
| S272R | 2.31 |
| S318N | 2.32 |
| T362C | 2.32 |
| N145F | 2.33 |

TABLE 2-continued

| Substitution using SEQ ID NO: 3 for numbering | AIF |
|---|---|
| I228V | 2.33 |
| D280M | 2.33 |
| A344L | 2.33 |
| I228F | 2.33 |
| G128R | 2.33 |
| S130I | 2.34 |
| A53L | 2.35 |
| G249C | 2.35 |
| S130N | 2.35 |
| S272I | 2.37 |
| K45Y | 2.37 |
| T146C | 2.38 |
| N338T | 2.38 |
| D110W | 2.39 |
| T213R | 2.39 |
| A319W | 2.39 |
| N124L | 2.40 |
| T146I | 2.40 |
| K305T | 2.40 |
| T27S | 2.41 |
| T288V | 2.41 |
| S66T | 2.43 |
| S29L | 2.44 |
| L136C | 2.44 |
| N145R | 2.46 |
| G141V | 2.46 |
| A34L | 2.46 |
| K305F | 2.47 |
| G141C | 2.47 |
| A184W | 2.47 |
| N338S | 2.47 |
| A184F | 2.48 |
| A184I | 2.50 |
| S306L | 2.50 |
| N153Y | 2.50 |
| N145V | 2.51 |
| T362H | 2.51 |
| M200L | 2.51 |
| E117S | 2.51 |
| S317A | 2.52 |
| T93S | 2.53 |
| T362Y | 2.53 |
| T146M | 2.54 |
| A344K | 2.56 |
| S318R | 2.56 |
| S29R | 2.56 |
| T146R | 2.57 |
| N356L | 2.57 |
| T69C | 2.57 |
| F125K | 2.58 |
| Q154L | 2.59 |
| Y159H | 2.61 |
| P341I | 2.61 |
| V266R | 2.61 |
| G20R | 2.62 |
| V364M | 2.62 |
| G128S | 2.63 |
| G244N | 2.63 |
| G304R | 2.64 |
| I228L | 2.65 |
| S317H | 2.66 |
| G20L | 2.66 |
| A358L | 2.67 |
| Y231F | 2.67 |
| V209Y | 2.69 |
| K321S | 2.69 |
| G128Y | 2.69 |
| I277L | 2.70 |
| T362I | 2.71 |
| T146V | 2.71 |
| Q275R | 2.72 |
| I228Y | 2.72 |
| N145W | 2.72 |
| S210L | 2.72 |
| S29P | 2.74 |
| S237F | 2.74 |
| T213I | 2.75 |
| V261A | 2.76 |
| S272L | 2.76 |
| T146A | 2.78 |
| S60E | 2.78 |
| N115G | 2.79 |
| K305I | 2.79 |
| S237K | 2.79 |
| G141A | 2.80 |
| L308P | 2.81 |
| S29A | 2.81 |
| E81S | 2.82 |
| S66M | 2.83 |
| L127P | 2.83 |
| S29C | 2.83 |
| G208H | 2.83 |
| P101F | 2.84 |
| L96T | 2.84 |
| P101R | 2.85 |
| G304K | 2.85 |
| A46E | 2.87 |
| N115D | 2.88 |
| F125M | 2.88 |
| T103V | 2.88 |
| N145G | 2.89 |
| F199L | 2.89 |
| S336R | 2.90 |
| D280N | 2.91 |
| S62N | 2.91 |
| F55R | 2.91 |
| V209N | 2.94 |
| G304S | 2.95 |
| V209G | 2.95 |
| G208Y | 2.96 |
| S50L | 2.97 |
| Q275K | 2.97 |
| P348G | 2.98 |
| S61P | 3.00 |
| N145I | 3.00 |
| D267S | 3.01 |
| G128W | 3.02 |
| G128N | 3.03 |
| D280S | 3.04 |
| N124I | 3.05 |
| D76V | 3.06 |
| S130F | 3.07 |
| S237L | 3.15 |
| T102C | 3.18 |
| V327C | 3.19 |
| V209L | 3.22 |
| S317G | 3.23 |
| G304H | 3.24 |
| L96S | 3.24 |
| S272Y | 3.24 |
| D280F | 3.25 |
| D76G | 3.27 |
| T167D | 3.28 |
| A319F | 3.30 |
| Q142A | 3.32 |
| E117D | 3.34 |
| Y159S | 3.34 |
| T102I | 3.34 |
| Y231S | 3.37 |
| G141Q | 3.39 |
| T98L | 3.41 |
| K305H | 3.45 |
| Q182F | 3.45 |
| P101M | 3.50 |
| S272T | 3.52 |
| S317Y | 3.54 |
| N124K | 3.58 |
| P101L | 3.60 |
| S130D | 3.60 |
| T146W | 3.62 |
| T276V | 3.64 |
| S237I | 3.66 |
| N145S | 3.70 |
| G304P | 3.73 |
| F125L | 3.77 |
| N115A | 3.78 |

TABLE 2-continued

| Substitution using SEQ ID NO: 3 for numbering | AIF |
|---|---|
| P348S | 3.83 |
| G141R | 3.84 |
| P341N | 3.86 |
| D326P | 3.89 |
| G345K | 3.90 |
| I59M | 3.92 |
| D76P | 3.97 |
| V209F | 3.98 |
| D280T | 4.08 |
| N356Y | 4.08 |
| S29N | 4.14 |
| L361P | 4.15 |
| L96F | 4.17 |
| S317C | 4.21 |
| P341R | 4.21 |
| S60P | 4.22 |
| D109P | 4.26 |
| S317L | 4.32 |
| G141F | 4.33 |
| I228Q | 4.38 |
| N124V | 4.38 |
| G141L | 4.56 |
| A34R | 4.56 |
| D76K | 4.62 |
| F310M | 4.65 |
| V209H | 4.67 |
| T146H | 4.71 |
| D76A | 4.73 |
| T276F | 4.74 |
| S317W | 4.81 |
| G141M | 4.82 |
| E117L | 4.83 |
| S317K | 4.86 |
| N87F | 4.86 |
| A34N | 4.92 |
| Q154R | 4.93 |
| D76L | 5.01 |
| E117G | 5.31 |
| F310P | 5.38 |
| D76Y | 5.65 |
| E117N | 5.70 |
| S317R | 5.79 |
| Q142S | 5.94 |
| S317I | 5.96 |
| A285S | 6.18 |
| N338H | 6.30 |
| G345S | 6.63 |
| D76N | 6.65 |
| T146N | 7.30 |
| S294T | 7.35 |
| E117P | 7.38 |
| E117W | 8.19 |
| Q142W | 9.44 |
| Q142M | 16.09 |
| Q142L | 18.97 |
| E117Y | 20.96 |
| E117F | 21.55 |

Example 4: Expression Level Determination for Specific Variants According to the Invention The expression levels of substitution variants of MgP3 relative to MgP3 having the amino acid sequence of SEQ ID NO: 3 is determined by the total amount of MgP3 protein in the culture supernatant. Using a system where precisely one copy of the variant is integrated into a defined locus, and said locus is identical for all variants, allows for direct comparison of expression levels between specific variants. Such a system could be the DSMS system described in example 1. The protein concentration was determined by enzyme-linked immunosorbent assay (ELISA), described below.

A.
Protein Quantification by Enzyme-Linked Immunosorbent Assay (ELISA)

The reagent solutions used are:

TBS-T: 20 mM Tris, 150 mM NaCl, 0.1% Tween-20, pH 7.5.

PBS buffer: 137 mM NaCl, 2.7 mM KCl, 10 mM $Na_2HPO_4$ 1.8 mM $KH_2PO_4$.

TMB plus 2 (KemEnTech diagnostics A/S) is pre-made and ready for use.

The protease sample (culture supernatant) was diluted 2000-fold in TBS-T and analyzed by ELISA, using a rabbit-raised HRP-conjugated MgP3-antibody. ELISA quantification is carried out in blocked 384 microtiter plate (Nunc MaxiSorp) coated with "protein A"-purified rabbit Polyclonal-anti-MgP3 antibodies. The diluted enzyme samples (as well as standards and controls) are transferred to the antibody-plate, incubated, and followed by repeated vigorous washing with PBS buffer. Detection is carried out using the same polyclonal antibodies, however in a HRP-labeled form (LL-HRP conjugation). Anti-MgP3:HRP conjugate in TBS-T in appropriate dilution is added, followed by PBS washing. Signal read as end-point OD-(620 nM) subsequent to TMB plus 2 substrate addition.

Concentrations were calculated from using a non-linear function that were derived from the MgP3-containing standard samples that were located on external plates, as well as MgP3 standard wells that were added to each plate in the screening flow.

Improvement Factor for Expression Level (EIF)

The expression level improvement factor (EIF) correlates the expression level of a variant protease with that of the reference protease. Calculation of the improvement factor EIF based on expression level (EL) was done according to the following equation: IF=(EL of the variant)/(EL of MgP3 (SEQ ID NO: 3)).

An expression level improvement factor that is greater than 1 (EIF>1) indicates an improved expression level of a variant as compared to the reference, while an EIF of 1 (EIF=1) identifies a variant which is on par with the reference, and an EIF of less than 1 (EIF<1) identifies a variant that has a lower expression level compared to the reference. The EIF of all mutations with improved expression levels is shown in the table 3 below. If a given substitution was observed more than once, the median EIF of all observations is shown.

TABLE 3

| Substitution using SEQ ID NO: 3 for numbering | EIF |
|---|---|
| S294G | 1.39 |
| A82H | 1.40 |
| T102H | 1.42 |
| S291V | 1.42 |
| P307T | 1.43 |
| T213S | 1.44 |
| T103V | 1.44 |
| A205S | 1.45 |
| G99V | 1.45 |
| T69F | 1.45 |
| V292S | 1.45 |
| T362R | 1.45 |
| S80G | 1.45 |
| T103F | 1.46 |
| S80N | 1.46 |
| V271S | 1.47 |
| A46L | 1.47 |
| S80L | 1.47 |
| T69A | 1.49 |

TABLE 3-continued

| Substitution using SEQ ID NO: 3 for numbering | EIF |
|---|---|
| F55L | 1.50 |
| I301T | 1.50 |
| V209P | 1.50 |
| T102A | 1.51 |
| T103I | 1.51 |
| N87P | 1.51 |
| C284A | 1.51 |
| T69Y | 1.51 |
| Q41T | 1.52 |
| T63V | 1.52 |
| Q207N | 1.52 |
| S62H | 1.52 |
| V271Y | 1.52 |
| T63G | 1.52 |
| T69P | 1.52 |
| T69R | 1.52 |
| D280Y | 1.53 |
| Y159F | 1.53 |
| Y159L | 1.53 |
| A363T | 1.53 |
| F55Y | 1.53 |
| P211F | 1.53 |
| V279I | 1.54 |
| A46W | 1.54 |
| I59K | 1.54 |
| S60I | 1.55 |
| S80T | 1.55 |
| S272N | 1.55 |
| S62I | 1.55 |
| S62R | 1.55 |
| K57H | 1.56 |
| I59R | 1.56 |
| F217I | 1.56 |
| M200L | 1.57 |
| S66G | 1.57 |
| K45S | 1.58 |
| Q41V | 1.58 |
| I169S | 1.58 |
| I84G | 1.58 |
| P211S | 1.58 |
| T98C | 1.59 |
| Q54V | 1.59 |
| S61A | 1.59 |
| T167L | 1.59 |
| F199Y | 1.60 |
| S329D | 1.61 |
| S329V | 1.61 |
| F314L | 1.61 |
| S331A | 1.61 |
| S331G | 1.61 |
| S331T | 1.61 |
| P333V | 1.61 |
| S336G | 1.61 |
| S336L | 1.61 |
| S336T | 1.61 |
| F55N | 1.61 |
| S60Y | 1.62 |
| S60L | 1.62 |
| T63E | 1.62 |
| S62L | 1.63 |
| T64D | 1.63 |
| S62V | 1.63 |
| G114C | 1.63 |
| F55T | 1.63 |
| I59V | 1.64 |
| V266S | 1.64 |
| V271F | 1.64 |
| T64C | 1.64 |
| V266F | 1.64 |
| A242E | 1.65 |
| S60Q | 1.66 |
| I270C | 1.66 |
| Q134A | 1.66 |
| K57V | 1.66 |
| Q54Y | 1.67 |
| Q269S | 1.67 |
| T64M | 1.68 |
| Q54S | 1.69 |
| V271K | 1.69 |
| Q54R | 1.69 |
| Q41L | 1.69 |
| V266Y | 1.70 |
| T167A | 1.72 |
| N115Y | 1.72 |
| S60R | 1.72 |
| S272A | 1.73 |
| A149D | 1.74 |
| E129V | 1.74 |
| I59D | 1.74 |
| G278S | 1.74 |
| T288A | 1.74 |
| T288C | 1.74 |
| T288G | 1.74 |
| V296P | 1.74 |
| V296R | 1.74 |
| V296T | 1.74 |
| T167S | 1.75 |
| S61F | 1.75 |
| I2L | 1.75 |
| Q269T | 1.76 |
| N131S | 1.76 |
| Q41Y | 1.77 |
| F42R | 1.77 |
| T167W | 1.78 |
| I270S | 1.79 |
| Q112H | 1.79 |
| N131V | 1.79 |
| A17P | 1.79 |
| P22V | 1.80 |
| E129S | 1.81 |
| T63A | 1.81 |
| I59S | 1.83 |
| Q269F | 1.83 |
| Q112R | 1.84 |
| T63R | 1.84 |
| D267T | 1.84 |
| K57L | 1.84 |
| Q269X | 1.84 |
| V266L | 1.85 |
| E129L | 1.87 |
| V266T | 1.87 |
| Q134L | 1.87 |
| G114P | 1.88 |
| V266A | 1.88 |
| V271M | 1.88 |
| G114A | 1.89 |
| Q269I | 1.90 |
| Q269V | 1.92 |
| I270A | 1.92 |
| Q269C | 1.93 |
| D267L | 1.95 |
| N131I | 1.95 |
| E129Y | 1.96 |
| Q112M | 1.97 |
| Q112S | 1.97 |
| I270L | 1.97 |
| V271I | 1.98 |
| D267F | 2.00 |
| G114L | 2.01 |
| G274R | 2.02 |
| Q134R | 2.03 |
| K250R | 2.08 |
| D267V | 2.13 |

Example 5: Variants Having Increased Thermo-Stability as Determined by Residual Activity for Specific Combinations of Substitutions after Thermal Stress Based on the data obtained for single substitution variants according to the invention, several variants having multiple substitutions and displaying an increase in residual activity after incubation at temperatures selected in the range from 56° C. to 70° C. for 20 min.

Variants, harboring substitutions compared to the wild-type MgP3 (SEQ ID NO: 3) as shown in Table 4, were constructed, and expressed in *A. oryzae*. The MgP3 *A. oryzae* strains harboring and expressing the MgP3 combination variants, were grown in microtiter plates (MTP) in MDU-2 (225 μL/MTP well) for expression, for 5 days at 30° C. in 96-well lidded MTP's without agitation. The expression plates also contained wild-type control MgP3 expressed in *A. oryzae*. The filamentous material was removed by pressing a Biopress® plate down into the wells. The supernatant was diluted in Assay buffer (100 mM Succinic acid, 1 mM $CaCl_2$, 150 mM KCl, 0.01% Triton X-100, pH 4.5). A fraction of the diluted supernatant was transferred to a thermocycler 96-well plate. The 96-well plate was transferred to a TRobot® Thermocycler (Biometra) and heated at temperatures annotated in Table 4 (56° C., 60° C. or 70° C.) for 20 min, followed by a cool-down to 25° C. for 2 min. Volumes (25 μL) of the stressed and unstressed supernatant were transferred to a transparent 384-well MTP plate. Assay solution (25 μL, Assay buffer, with 1 mM Succinyl-AAPF-pNA, 12.5 μL $mL^{-1}$ DMSO) is dispensed to the 384-well MTP. Absorbance was recorded at 405 nm for 10 minutes, and the initial rate was calculated per well from the maximum velocity of a window of 9 min. The ratio of initial rate of the stressed and non-stressed supernatants originating from the same clone were defined as $$\text{Ratio} = \frac{Vmax \text{ Stressed}}{Vmax \text{ Unstressed}},$$

which translates to residual activity (%), which is displayed in Table 4.

TABLE 4

Variants with multiple substitutions.

| Variant name | Substitutions compared to mature MgP3 of SEQ ID NO: 3 | Residual activity 56° C. | Residual activity 60° C. | Residual activity 70° C. |
|---|---|---|---|---|
| DMKP1163 (Wild-type/ SEQ ID NO: 3) | N/A | 40% | 0% | 0% |
| DMgP025-B | I39L + S66T + T102V | 100% | N/D | 21% |
| DMgP025-C | I39L + S66T + T102V + D267N S272Y + D280S | 100% | N/D | 12% |
| DMgP026-B | I39L + K57P + I59M + S66T + T102V F111H + N115K + D267N + S272Y | 88% | N/D | 37% |
| DMgP044 | I39L + K57P + I59M + S66T + T102V + F111H + N115K + D280S | 100% | 100% | 13% |
| DMgP045 | D267N + S272Y + Q275K + D280S | 100% | 100% | 0% |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A protease variant, comprising a substitution at one or more positions corresponding to positions 1, 5, 9, 25, 29, 30, 32, 38, 39, 40, 41, 42, 45, 46, 49, 50, 53, 54, 55, 57, 59, 60, 61, 62, 64, 67, 68, 69, 74, 76, 77, 78, 79, 80, 81, 82, 87, 93, 94, 96, 99, 102, 103, 105, 109, 111, 112, 114, 115, 117, 122, 123, 124, 128, 130, 136, 141, 142, 145, 146, 147, 150, 153, 154, 157, 159, 161, 167, 169, 175, 182, 185, 199, 200, 205, 207, 209, 210, 213, 216, 217, 225, 228, 231, 234, 237, 242, 244, 245, 246, 248, 258, 262, 266, 267, 269, 271, 272, 276, 278, 280, 284, 289, 293, 296, 299, 305, 308, 313, 314, 317, 318, 319, 321, 322, 324, 325, 326, 329, 330, 331, 333, 336, 338, 341, 343, 345, 347, 348, 355, 358, 359, 361, 362, 363, and 364 of the polypeptide of SEQ ID NO: 3, and the variant has protease activity and wherein the variant has at least 90%, but less than 100% sequence identity to the mature polypeptide of SEQ ID NO: 3, and wherein the variant has increased thermo-stability measured as improvement factor, HIF, compared to the protease of SEQ ID NO: 3, wherein the at least one substitution is selected from the group consisting of: A1T, S5I, S5K, S5L, S5Y, T9H, K25P, S29I, S29P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, A46E, K49P, S50C, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74H, E74R, D76L, D76R, Q77L, S78D, P79Y, S80L, E81A, E81H, E81K, E81L, E81P, E81Y, A82F, A82L, A82M, A82P, N87S, T93L, T93S, V94S, L96W, G99C, T102L, T102V, T103I, T103K, T103V, I105Q, D109H, D109K, D109M, D109Y, F111H, F111K, F111S, F111Y, Q112R, G114L, N115A, N115C, N115K, N115P, N115R, N115T, N115Y, E117D, E117G, E117H, E117N, E117Q, E117S, I122K, I122R, I123A, N124L, N124V, G128A, G128E, G128F, G128L, G128S, S130D, S130G, S130L, S130N, S130P, L136K, G141T, Q142A, Q142F, Q142L, Q142N, N145V, T146A, T146I, T146L, T146N, I147S, K150F, K150L, K150R, N153A, N153L, N153M, N153P, N153R, N153Y, Q154A, Q154I, Q154L, Q154M, Q154N, Q154T, Q154V, N157I, N157L, Y159H, Q161E, T167F, I169F, I169S, D175I, D175N, Q182C, Q182T, Q182V, H185P, F199L, F199M, M200S, A205S, Q207H, Q207L, V209F, S210T, T213L, T213R, A216R, F217I, F217N, V225Y, I228L, I228T, I228W, Y231I, S234Q, S237F, S237Q, A242I, A242L, A242V, G244S, S245P, T246S, S248Y, F258P, S262P, V266K, V266R, D267A, D267H, D267L, D267N, Q269L, V271R, S272I, S272K, S272L, S272R, S272T, S272V, S272Y, T276L, T276Y, G278P, D280N, D280S, D280T, D280Y, C284A, C284G, F289Y, I293T, V296A, V296I, R299N, K305S, L308V, P313L, F314I, F314L, S317E, S317N, S317W, S318P, A319F, A319Q, K321L, K321Q, K321S, A322D, L324Q, L324S, N325L, D326P, S329C, S329H, S329I, S329L, S329N, S329T, S329V, S329W, G330Q, S331W, S331Y, P333R, S336K, S336N, N338M, N338Q, N338R, P341S, K343A, K343H, K343S, K343T, K343V, G345S, D347I, P348Y, P355I, P355R, A358L, A358P, A358R, A358Y, K359L, K359S, L361M, T362L, T362N, A363G, A363L, and V364I, wherein the positions correspond to amino acid positions in the amino acid sequence set forth in SEQ ID NO: 3; and wherein the substitution at the one or more positions provides a protease variant having an increase in thermo-stability measured as improvement factor, HIF, of at least 1.4.

2. The variant of claim 1, which has at least 95%, but less than 100%, sequence identity to the amino acid sequence of SEQ ID NO: 3.

3. The variant of claim 1, wherein the number of substitutions is 1-20.

4. The variant of claim 1, comprising at least one substitution selected from the group consisting of: S5K, S5L, S5Y, T9H, K25P, S29R, S30E, K32W, F38L, I39G, I39L, I39V, I39Y, D40F, D40G, D40H, D40N, D40P, Q41I, Q41V, F42C, F42K, F42S, F42Y, K45L, K45M, K45Y, A46C, K49P, S50I, S50L, S50M, S50Q, A53C, A53E, A53V, Q54I, Q54L, Q54M, Q54V, F55H, F55L, K57P, K57S, I59G, I59M, I59P, S60P, S61L, S61P, S62C, S62N, S62P, T64G, T64I, L67V, Q68V, Q68Y, T69C, E74R, D76L, D76R, Q77L, S78D, P79Y, S80L, E81A, E81H, E81K, E81L, E81P, E81Y, A82M, A82P, N87S, T93L, V94S, G99C, T102L, T102V, T103I, T103K, T103V, I105Q, D109H, D109K, D109M, D109Y, F111H, F111K, F111S, Q112R, G114L, N115C, N115K, N115R, N115T, N115Y, E117D, E117G, E117H, E117N, E117Q, E117S, I122R, N124L, G128F, G128S, S130G, S130N, S130P, L136K, G141T, Q142A, Q142F, Q142L, Q142N, N145V, T146A, T146I, T146L, T146N, I147S, K150L, N153M, N153P, N153R, Q154I, Q154L, Q154N, Q154T, Q154V, N157L, Q161E, T167F, I169F, D175N, Q182C, Q182T, Q182V, F199L, F199M, M200S, A205S, Q207H, Q207L, V209F, S210T, T213R, F217I, V225Y, I228L, I228T, I228W, S234Q, S237F, G244S, S245P, T246S, S248Y, F258P, S262P, V266K, V266R, D267A, D267H, D267L, D267N, Q269L, V271R, S272K, S272L, S272R, S272V, S272Y, T276Y, G278P, D280N, D280S, D280T, C284G, F289Y, I293T, V296A, R299N, K305S, L308V, F314L, S317E, S317W, S318P, A319F, A319Q, K321L, K321Q, K321S, A322D, L324Q, L324S, D326P, S329C, S329H, S329I, S329L, S329N, S329W, G330Q, S331W, S331Y, S336K, S336N, P341S, K343A, K343H, K343S, K343T, G345S, D347I, P348Y, P355I, A358L, A358P, A358R, A358Y, K359L, K359S, L361M, T362L, A363G, A363L, and V364I, wherein the substitution at the one or more positions provides a protease variant having an increase in thermo-stability measured as improvement factor, HIF, of at least 1.6.

5. A composition comprising a variant of claim 1.

6. A process for producing a fermentation product from starch-containing material comprising simultaneously saccharifying and fermenting starch-containing material using carbohydrate-source generating enzymes and a fermenting organism at a temperature below the initial gelatinization temperature of said starch-containing material in the presence of a variant protease of claim 1.

7. The process of claim 6, wherein the fermentation product is ethanol.

8. A process for producing a fermentation product from starch-containing material comprising the steps of:
(a) liquefying starch-containing material in the presence of an alpha-amylase;
(b) saccharifying the liquefied material obtained in step (a) using a glucoamylase; and
(c) fermenting using a fermenting organism;
wherein a variant protease of claim 1 is present during step b) and/or c).

9. The process of claim 8, wherein the fermentation product is ethanol.

10. A protease variant, comprising a substitution at one or more positions corresponding to positions 20, 27, 29, 34, 40, 42, 45, 46, 50, 53, 54, 55, 58, 59, 60, 61, 62, 66, 69, 76, 81, 87, 93, 96, 98, 101, 102, 103, 109, 110, 115, 117, 122, 124, 125, 127, 128, 130, 136, 141, 142, 145, 146, 148, 149, 150, 153, 154, 157, 159, 161, 164, 167, 182, 183, 184, 185, 188, 199, 200, 207, 208, 209, 210, 211, 213, 216, 219, 228, 231, 237, 244, 249, 252, 253, 261, 266, 267, 272, 275, 276, 277, 280, 285, 288, 291, 292, 293, 294, 296, 299, 303, 304, 305, 306, 307, 308, 310, 317, 318, 319, 321, 326, 327, 336, 338, 341, 344, 345, 348, 356, 358, 359, 361, 362, 363, and 364 of the polypeptide of SEQ ID NO: 3, and the variant has protease activity and wherein the variant has at least 90%, but less than 100% sequence identity to the mature polypeptide of SEQ ID NO: 3, wherein the at least one substitution is selected from the group consisting of: G20L, G20R, T27S, S29A, S29C, S29L, S29N, S29P, S29R, A34L, A34N, A34R, D40S, D40Y, F42Y, K45L, K45Y, A46E, A46K, 550A, S50C, S50I, S50L, S50T, A53I, A53K, A53L, A53S, Q54L, F55R, D58M, I59M, I59P, 560C, S60E, S60P, S61D, S61P, S62C, S62N, S66F, S66L, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, I122L, N124D, N124I, N124K, N124L, N124M, N124T, N124V, F125K, F125L, F125M, L127C, L127P, G128N, G128R, G128S, G128W, G128Y, S130D, S130F, S130I, S130N, L136C, G141A, G141C, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T1460, T146H, T146I, T146M, T146N, T146Q, T146R, T146V, T146W, S148G, A149V, K150F, N153Y, N153F, N153D, N153G, N153R, N153Y, Q154C, Q154F, Q154G, Q154I, Q154K, Q154L, Q154M, Q154R, Q154T, Q154V, Q154W, Q154Y, N157A, N157E, N157F, N157M, N157Y, Y159F, YI59G, Y159H, Y159S, Q161A, A164L, T167D, T167V, Q182F, S183A, S183F, S183L, S183M, A184D, A184F, A184H, A184I, A184K, A184L, A184Q, A184R, A184S, A184T, A184V, A184W, A184Y, H185A, H185L, H185P, H185S, N188L, N188Q, F199L, M200F, M200L, Q207F, G208H, G208Y, V209F, V209G, V209H, V209L, V209N, V209W, V209Y, S210E, S210L, S210R, S210T, S210Y, P211F, T213F, T213H, T213I, T213L, T213N, T213R, T213S, T213W, T213Y, A216F, A216L, S219M, I228F, I228H, I228L, I228M, I228Q, I228V, I228Y, Y231F, Y231S, S237F, S237I, S237K, S237L, G244L, G244N, G244P, G244R, G249C, N252F, N252K, N252S, R253C, V261A, V261G, V266C, V266R, D267S, S272I, S272K, S272L, S272M, S272Q, S272R, S272T, S272Y, Q275A, Q275F, Q275K, Q275L, Q275R, Q275V, T276F, T276R, T276V, I277L, I277V, D280F, D280H, D280M, D280N, D280S, D280T, A285L, A285S, T288C, T288I, T288V, S291V, V292C, I293M, I293Y, S294T, S294V, V296L, R299P, A303C, A303F, A303H, A303S, A303V, G304H, G304K, G304P, G304R, G304S, G304Y, K3050, K305F, K305H, K305I, K305L, K305M, K305S, K305T, K305Y, S306L, S306M, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327T, S336N, N338H, N338S, N338T, P341I, P341N, P341R, A344K, A344L, A344P, G345K, G345S, P348G, P348L, P348S, N356L, N356Y, A358F, A358L, A358P, K359C, K359L, K359S, K359W, L361E, L361M, L361P, L361R, L361S, L361T, L361V, T362A, T362C, T362H, T362I, T362K, T362L, T362M, T362P, T362Q, T362R, T362V, T362Y, A363E, A363F, A363L, A363M, A363V, V364F, V364I, V364L, V364M, and V364S, and wherein the substitution at the one or more positions provides a protease variant having an increase in specific activity measured as improvement factor, AIF, of at least 1.37.

11. The variant of claim 10, which has at least 95%, but less than 100%, sequence identity to the amino acid sequence of SEQ ID NO: 3.

12. The variant of claim 10, wherein the number of substitutions is 1-20.

13. The variant of claim 10, comprising at least one substitution selected from the group consisting of: G20L, G20R, T27S, S29A, S29C, S29L, S29N, S29P, S29R, A34L, A34N, A34R, F42Y, K45L, K45Y, A46E, A46K, S50A, S50L, A53L, Q54L, F55R, I59M, I59P, S60E, S60P, S61D, S61P, S62N, S66M, S66T, T69C, D76A, D76G, D76K, D76L, D76N, D76P, D76V, D76Y, E81S, N87F, T93S, L96F, L96S, L96T, T98L, P101F, P101L, P101M, P101R, T102C, T102I, T103V, D109P, D110W, N115A, N115D, N115G, N115P, E117D, E117F, E117G, E117L, E117N, E117P, E117S, E117W, E117Y, N124D, N124I, N124K, N124L, N124M, N124T, N124V, F125K, F125L, F125M, L1270, L127P, G128N, G128R, G128S, G128W, G128Y, S130D, S130F, S130I, S130N, L1360, G141A, G1410, G141F, G141L, G141M, G141Q, G141R, G141V, Q142A, Q142L, Q142M, Q142S, Q142W, N145F, N145G, N145I, N145L, N145P, N145R, N145S, N145V, N145W, T146A, T1460, T146H, T146I, T146M, T146N, T146Q, T146R, T146V, T146W, S148G, A149V, K150F, N153Y, Q154I, Q154K, Q154L, Q154M, Q154R, Q154W, N157F, N157Y, Y159H, Y159S, Q161A, T167D, Q182F, A184F, A184I, A184K, A184V, A184W, H185A, N188L, F199L, M200F, M200L, Q207F, G208H, G208Y, V209F, V209G, V209H, V209L, V209N, V209W, V209Y, S210E, S210L, S210R, S210T, S210Y, P211F, T213F, T213I, T213L, T213N, T213R, T213S, T213W, A216F, S219M, I228F, I228H, I228L, I228M, I228Q, I228V, I228Y, Y231F, Y231S, S237F, S237I, S237K, S237L, G244N, G249C, N252F, V261A, V261G, V266C, V266R, D267S, S272I, S272L, S272M, S272Q, S272R, S272T, S272Y, Q275F, Q275K, Q275L, Q275R, Q275V, T276F, T276R, T276V, I277L, I277V, D280F, D280H, D280M, D280N, D280S, D280T, A285S, T288C, T288V, I293Y, S294T, S294V, A303F, G304H, G304K, G304P, G304R, G304S, K305O, K305F, K305H, K305I, K305S, K305T, S306L, S306R, P307C, L308P, L308T, F310M, F310P, F310Y, S317A, S317C, S317G, S317H, S317I, S317K, S317L, S317R, S317W, S317Y, S318N, S318R, A319F, A319W, K321R, K321S, D326P, V327C, V327R, S336R, N338H, N338S, N338T, P341I, P341N, P341R, A344K, A344L, A344P, G345K, G345S, P348G, P348L, P348S, N356L, N356Y, A358L, K359S, K359W, L361P, L361R, T362C, T362H, T362I, T362K, T362M, T362R, T362Y, A363F, and V364M, wherein the substitution at the one or more positions provides a protease variant having an increase in specific activity measured as improvement factor, AIF, of at least 2.0.

14. The variant of claim 10, comprising at least one substitution selected from the group consisting of G20L, G20R, S29A, S29C, S29N, S29P, A34N, A34R, A46E, S50L, F55R, I59M, S60E, S60P, S61P, S62N, S66M, D76A, D76G, D76K, D76L, D76N, D76P, D76V, D76Y, E81S, N87F, L96F, L96S, L96T, T98L, P101F, P101L, P101M, P101R, T102C, T102I, T103V, D109P, N115A, N115D, N115G, E117D, E117F, E117G, E117L, E117N, E117P, E117W, E117Y, N124I, N124K, N124V, F125L, F125M, L127P, G128N, G128S, G128W, G128Y, S130D, S130F, G141A, G141F, G141L, G141M, G141Q, G141R, Q142A, Q142L, Q142M, Q142S, Q142W, N145G, N145I, N145S, N145W, T146A, T146H, T146N, T146V, T146W, Q154R, Y159H, Y159S, T167D, Q182F, F199L, G208H, G208Y, V209F, V209G, V209H, V209L, V209N, V209Y, S210L, T213I, I228L, I228Q, I228Y, Y231F, Y231S, S237F, S237I, S237K, S237L, G244N, V261A, V266R, D267S, S272L, S272T, S272Y, Q275K, Q275R, T276F, T276V, I277L, D280F, D280N, D280S, D280T, A285S, S294T, G304H, G304K, G304P, G304R, G304S, K305H, K305I, L308P, F310M, F310P, S317C, S317G, S317H, S317I, S317K, S317L, S317R, S317W, S317Y, A319F, K321S, D326P, V327C, S336R, N338H, P341I, P341N, P341R, G345K, G345S, P348G, P348S, N356Y, A358L, L361P, T362I, and V364M, wherein the substitution at the one or more positions provides a protease variant having an increase in specific activity measured as improvement factor, AIF, of at least 2.6.

15. The variant of claim 10, comprising at least one substitution selected from the group consisting of A34N, A34R, D76A, D76K, D76L, D76N, D76Y, N87F, E117F, E117G, E117L, E117N, E117P, E117W, E117Y, G141L, G141M, Q142L, Q142M, Q142S, Q142W, T146H, T146N, Q154R, V209H, T276F, A285S, S294T, F310M, F310P, S317I, S317K, S317R, S317W, N338H, and G345S, wherein the substitution at the one or more positions provides a protease variant having an increase in specific activity measured as improvement factor, AIF, of at least 4.5.

16. The variant of claim 10, wherein the variant comprises a substitution selected from the group consisting of I39L, K57P, I59M, S66T, T102V, F111H, N115K, D267N, S272Y, Q275K, and D280S.

17. The variant of claim 16, wherein the variant has increased thermo-stability measured as residual activity after thermal stress for 20 min at 56° C.

18. The variant of claim 17, wherein the residual activity is at least 50%.

19. The variant of claim 10, wherein the variant comprises at least three substitutions selected from the group consisting of I39L, K57P, I59M, S66T, T102V, F111H, N115K, D267N, S272Y, Q275K, and D280S.

20. The variant of claim 19, comprising the substitutions I39L+S66T+T102V or D267N+S272Y+Q275K+D280S.

21. The variant of any of claim 19, comprising the substitutions:
I39L+S66T+T102V;
I39L+S66T+T102V+D267N S272Y+D280S;
I39L+K57P+I59M+S66T+T102V F111H+N115K+ D267N+S272Y,
I39L+K57P+I59M+S66T+T102V+F111H+N115K+ D280S; or
D267N+S272Y+Q275K+D280S.

22. A composition comprising a variant of claim 10.

23. A process for producing a fermentation product from starch-containing material comprising simultaneously saccharifying and fermenting starch-containing material using carbohydrate-source generating enzymes and a fermenting organism at a temperature below the initial gelatinization temperature of said starch-containing material in the presence of a variant protease of claim 10.

24. The process of claim 23, wherein the fermentation product is ethanol.

25. A process for producing a fermentation product from starch-containing material comprising the steps of:
(a) liquefying starch-containing material in the presence of an alpha-amylase;
(b) saccharifying the liquefied material obtained in step (a) using a glucoamylase; and
(c) fermenting using a fermenting organism;
wherein a variant protease of claim 10 is present during step b) and/or c).

26. The process of claim 25, wherein the fermentation product is ethanol.

27. A protease variant, comprising at least one substitution corresponding to positions 2, 17, 22, 41, 41, 42, 45, 46, 54, 55, 57, 59, 60, 61, 62, 63, 64, 66, 69, 80, 82, 84, 87, 98, 99, 102, 103, 112, 114, 115, 129, 131, 134, 149, 159, 167, 169, 199, 200, 205, 207, 209, 211, 213, 217, 242, 250, 266, 267, 269, 270, 271, 272, 274, 278, 279, 280, 284, 288, 291, 292, 294, 296, 301, 307, 314, 329, 331, 333, 336, 362, and 363 of the polypeptide of SEQ ID NO: 3, and the variant has protease activity and wherein the variant has at least 90%, but less than 100% sequence identity to the mature polypeptide of SEQ ID NO: 3, and wherein the substitution at one or more positions is selected from the group consisting of I2L, A17P, P22V, Q41L, Q41T, Q41V, Q41Y, F42R, K45S, A46L, A46W, Q54R, Q54S, Q54V, Q54Y, F55L, F55N, F55T, F55Y, K57H, K57L, K57V, I59D, I59K, I59R, I59S, I59V, S60I, S60L, S60Q, S60R, S60Y, S61A, S61F, S62H, S62I, S62L, S62R, S62V, T63A, T63E, T63G, T63R, T63V, T64C, T64D, T64M, S66G, T69A, T69F, T69P, T69R, T69Y, S80G, S80L, S80N, S80T, A82H, I84G, N87P, T98C, G99V, T102A, T102H, T103F, T103I, T103V, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, Y159F, Y159L, T167A, T167L, T167S, T167W, 1169S, F199Y, M200L, A205S, Q207N, V209P, P211L, P211S, T213S, F217I, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, I270S, V271F, V271I, V271K, V271M, V271S, V271Y, S272A, S272N, G274R, G278S, V279I, D280Y, C284A, T288A, T288C, T288G, S291V, V292S, S294G, V296P, V296R, V296T, I301T, P307T, F314L, S329D, S329V, S331A, S331G, S331T, P333V, S336G, S336L, S336T, T362R, and A363T, and wherein the substitution at the one or more positions provides a protease variant having an increase in expression level in *Aspergillus oryzae* measured as improvement factor, EIF, of at least 1.38.

28. The variant of claim 27, which has at least 95%, but less than 100%, sequence identity to the amino acid sequence of SEQ ID NO: 3.

29. The variant of claim 27, wherein the number of substitutions is 1-20.

30. The variant of claim 27, comprising at least one substitution selected from the group consisting of: I2L, A17P, P22V, Q41L, Q41Y, F42R, Q54R, Q54S, Q54Y, F55N, F55T, K57L, K57V, I59D, I59S, I59V, S60L, S60Q, S60R, S60Y, S61F, S62L, S62V, T63A, T63E, T63R, T64C, T64D, T64M, Q112H, Q112M, Q112R, Q112S, G114A, G114C, G114L, G114P, N115Y, E129L, E129S, E129V, E129Y, N131I, N131S, N131V, Q134A, Q134L, Q134R, A149D, T167A, T167S, T167W, F199Y, A242E, K250R, V266A, V266F, V266L, V266S, V266T, V266Y, D267F, D267L, D267T, D267V, Q269C, Q269F, Q269I, Q269S, Q269T, Q269V, Q269X, I270A, I270C, I270L, I270S, V271F, V271I, V271K, V271M, S272A, G274R, G278S, T288A, T288C, T288G, V296P, V296R, V296T, F314L, S329D, S329V, S331A, S331G, S331T, P333V, S336G, S336L, and S336T, wherein the substitution at the one or more positions provides a protease variant having an increase in expression level measured as improvement factor, EIF, of at least 1.6.

31. A composition comprising a variant of claim 27.

32. A process for producing a fermentation product from starch-containing material comprising simultaneously saccharifying and fermenting starch-containing material using carbohydrate-source generating enzymes and a fermenting organism at a temperature below the initial gelatinization temperature of said starch-containing material in the presence of a variant protease of claim 27.

33. The process of claim 32, wherein the fermentation product is ethanol.

34. A process for producing a fermentation product from starch-containing material comprising the steps of:
   (a) liquefying starch-containing material in the presence of an alpha-amylase;
   (b) saccharifying the liquefied material obtained in step (a) using a glucoamylase; and
   (c) fermenting using a fermenting organism;
   wherein a variant protease of claim 32 is present during step b) and/or c).

35. The process of claim 34, wherein the fermentation product is ethanol.

* * * * *

UNITED STATES PATENT AND TRADEMARK OFFICE
CERTIFICATE OF CORRECTION

PATENT NO. : 11,891,645 B2
APPLICATION NO. : 16/318509
DATED : February 6, 2024
INVENTOR(S) : Klitgaard et al.

It is certified that error appears in the above-identified patent and that said Letters Patent is hereby corrected as shown below:

In the Claims

Claim 1:
Column 105, Line 62, delete "5210T" and insert -- S210T --.

Claim 4:
Column 106, Line 59, delete "1169F" and insert -- I169F --.

Claim 10:
Column 107, Line 48, delete "550A" and insert -- S50A --.
Column 107, Line 49, delete "560C" and insert -- S60C --.
Column 107, Line 62, delete "T1460" and insert -- T146C --.
Column 108, Line 62, delete "K3050" and insert -- K305C --.

Claim 13:
Column 108, Line 54, delete "L1270" and insert -- L127C --.
Column 108, Line 55, delete "G1410" and insert -- G141C --.
Column 108, Line 59, delete "T1460" and insert -- T146C --.
Column 109, Line 55, delete "K3050" and insert -- K305C --.

Signed and Sealed this
Seventeenth Day of September, 2024

Katherine Kelly Vidal
*Director of the United States Patent and Trademark Office*

SEQUENCE LISTING

<160> NUMBER OF SEQ ID NOS: 12

<210> SEQ ID NO 1
<211> LENGTH: 1695
<212> TYPE: DNA
<213> ORGANISM: Meripilus giganteus

<400> SEQUENCE: 1

```
atggtcgcca ccagcttgct cgttgcctcc ctattcacgc tcgccctcgg cacgccgacg      60
ggtcgcaacc tcaagctgca cgaggcgcgc gaagaccttc ctgccggttt ctcgctgcgc     120
ggcgccgcct cgcccgacac gacgctgaag ctccgcatcg cgctcgtgca gaacaacttc     180
gccgagctcg aagacaagct ctacgacgtc agcacaccgt ccagcgccaa ctacggcaac     240
cacctctcga aggaagaggt tgagcagtac attgctccgg ctcccgagag cgtgaaagcc     300
gtgaatgcct ggctcaccga gaacggactc gacgcgcaca ccatttcgcc cgccggcgac     360
tggctcgcat tcgaggtccc cgtcagcaag gcgaatgagc tcttcgacgc cgacttctcc     420
gtgtttaccc acgatgagtc cggcctcgag gctatccgga cgctggccta ctccatccct     480
gctgagcttc agggacacct cgaccttgtt caccccaccg tcacgttccc gaacccaat     540 gcgcacctgc ccgtcgtgcg ctccacccag cccatccgga acctgaccgg acgtgctata     600
ccggcctctt gcgcgagcac catcacccct gcgtgcttgc aggccatcta cggtatcccc     660
accaccaagg ctactcagtc ctcgaacaag ctcgctgtca gcggcttcat cgaccagttt     720
gcgaacaagg ctgacctgaa gtcattcctg gcccagttcc gcaaagacat ctcatcctcc     780
acgactttct cgcttcagac tctcgatggt ggagagaacg accagagccc tagcgaggcg     840
```

```
ggtatcgagg ctaacttgga tatccagtac accgtcggcc tcgccacggg cgtccctacc    900
acgttcatct ccgtcggcga cgacttccag gatggcaact tggagggctt cctggacatc    960
atcaacttct tgctcggcga gagcaacccg ccgcaggtcc tcaccaccag ttacggccag   1020
aacgagaaca cgatctcggc caagcttgct aaccaacttt gcaatgcgta cgctcagctc   1080
ggcgcgcgcg gcacctctat cctcttcgcg tcgggtgatg gcggtgtgtc cggctcgcag   1140
tccgcgcact gcagcaattt tgtcccgaca ttccccctccg gctgcccctt catgacttcc   1200
gtcggcgcga cgcagggcgt cagccccgag actgccgccg ccttctcatc cggcggcttc   1260
tcgaacgtgt tcggcatccc cgtcgtaccag gcttccgcgg tcagcggcta cctgtccgcg   1320
ctcggaagca cgaactcggg caagttcaac cgcagcggac gcggattccc cgacgtctcc   1380
acgcaaggcg tggacttcca gatcgtcagc ggcggccaga cgatcggcgt cgacggcacg   1440
agctgcgcca gcccgacgtt cgcgagcgtc atctcgctgg taaacgaccg cctcatcgcg   1500
gccggcaaga gcccgctcgg cttcctgaac cccttcctgt actcgtcggc gggcaaggcc   1560
gcgctcaacg acgtcacgag tggctcgaac cctggctgca gcacgaacgg cttccccgct   1620
aaggccggct gggacccggt cactggtctt ggcacgccca actttgccaa gctcctcacc   1680
gcggtcggcc tgtga                                                    1695

<210> SEQ ID NO 2
<211> LENGTH: 564
<212> TYPE: PRT
<213> ORGANISM: Meripilus giganteus

<400> SEQUENCE: 2

Met Val Ala Thr Ser Leu Leu Val Ala Ser Leu Phe Thr Leu Ala Leu
1               5                   10                  15

Gly Thr Pro Thr Gly Arg Asn Leu Lys Leu His Glu Ala Arg Glu Asp
            20                  25                  30

Leu Pro Ala Gly Phe Ser Leu Arg Gly Ala Ala Ser Pro Asp Thr Thr
        35                  40                  45

Leu Lys Leu Arg Ile Ala Leu Val Gln Asn Asn Phe Ala Glu Leu Glu
    50                  55                  60

Asp Lys Leu Tyr Asp Val Ser Thr Pro Ser Ser Ala Asn Tyr Gly Asn
65                  70                  75                  80

His Leu Ser Lys Glu Glu Val Glu Gln Tyr Ile Ala Pro Ala Pro Glu
                85                  90                  95

Ser Val Lys Ala Val Asn Ala Trp Leu Thr Glu Asn Gly Leu Asp Ala
            100                 105                 110

His Thr Ile Ser Pro Ala Gly Asp Trp Leu Ala Phe Glu Val Pro Val
        115                 120                 125

Ser Lys Ala Asn Glu Leu Phe Asp Ala Asp Phe Ser Val Phe Thr His
    130                 135                 140

Asp Glu Ser Gly Leu Glu Ala Ile Arg Thr Leu Ala Tyr Ser Ile Pro
145                 150                 155                 160

Ala Glu Leu Gln Gly His Leu Asp Leu Val His Pro Thr Val Thr Phe
                165                 170                 175

Pro Asn Pro Asn Ala His Leu Pro Val Val Arg Ser Thr Gln Pro Ile
            180                 185                 190

Arg Asn Leu Thr Gly Arg Ala Ile Pro Ala Ser Cys Ala Ser Thr Ile
        195                 200                 205

Thr Pro Ala Cys Leu Gln Ala Ile Tyr Gly Ile Pro Thr Thr Lys Ala
```

```
                210                 215                 220
Thr Gln Ser Ser Asn Lys Leu Ala Val Ser Gly Phe Ile Asp Gln Phe
225                 230                 235                 240

Ala Asn Lys Ala Asp Leu Lys Ser Phe Leu Ala Gln Phe Arg Lys Asp
                245                 250                 255

Ile Ser Ser Ser Thr Thr Phe Ser Leu Gln Thr Leu Asp Gly Gly Glu
                260                 265                 270

Asn Asp Gln Ser Pro Ser Glu Ala Gly Ile Glu Ala Asn Leu Asp Ile
            275                 280                 285

Gln Tyr Thr Val Gly Leu Ala Thr Gly Val Pro Thr Thr Phe Ile Ser
        290                 295                 300

Val Gly Asp Asp Phe Gln Asp Gly Asn Leu Glu Gly Phe Leu Asp Ile
305                 310                 315                 320

Ile Asn Phe Leu Leu Gly Glu Ser Asn Pro Pro Gln Val Leu Thr Thr
                325                 330                 335

Ser Tyr Gly Gln Asn Glu Asn Thr Ile Ser Ala Lys Leu Ala Asn Gln
                340                 345                 350

Leu Cys Asn Ala Tyr Ala Gln Leu Gly Ala Arg Gly Thr Ser Ile Leu
            355                 360                 365

Phe Ala Ser Gly Asp Gly Gly Val Ser Gly Ser Gln Ser Ala His Cys
        370                 375                 380

Ser Asn Phe Val Pro Thr Phe Pro Ser Gly Cys Pro Phe Met Thr Ser
385                 390                 395                 400

Val Gly Ala Thr Gln Gly Val Ser Pro Glu Thr Ala Ala Ala Phe Ser
                405                 410                 415

Ser Gly Gly Phe Ser Asn Val Phe Gly Ile Pro Ser Tyr Gln Ala Ser
                420                 425                 430

Ala Val Ser Gly Tyr Leu Ser Ala Leu Gly Ser Thr Asn Ser Gly Lys
            435                 440                 445

Phe Asn Arg Ser Gly Arg Gly Phe Pro Asp Val Ser Thr Gln Gly Val
        450                 455                 460

Asp Phe Gln Ile Val Ser Gly Gly Gln Thr Ile Gly Val Asp Gly Thr
465                 470                 475                 480

Ser Cys Ala Ser Pro Thr Phe Ala Ser Val Ile Ser Leu Val Asn Asp
                485                 490                 495

Arg Leu Ile Ala Ala Gly Lys Ser Pro Leu Gly Phe Leu Asn Pro Phe
            500                 505                 510

Leu Tyr Ser Ser Ala Gly Lys Ala Ala Leu Asn Asp Val Thr Ser Gly
        515                 520                 525

Ser Asn Pro Gly Cys Ser Thr Asn Gly Phe Pro Ala Lys Ala Gly Trp
530                 535                 540

Asp Pro Val Thr Gly Leu Gly Thr Pro Asn Phe Ala Lys Leu Leu Thr
545                 550                 555                 560

Ala Val Gly Leu

<210> SEQ ID NO 3
<211> LENGTH: 366
<212> TYPE: PRT
<213> ORGANISM: Meripilus giganteus

<400> SEQUENCE: 3

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
```

```
                    20                  25                  30

Leu Ala Val Ser Gly Phe Ile Asp Gln Phe Ala Asn Lys Ala Asp Leu
            35                  40                  45

Lys Ser Phe Leu Ala Gln Phe Arg Lys Asp Ile Ser Ser Ser Thr Thr
 50                  55                  60

Phe Ser Leu Gln Thr Leu Asp Gly Gly Glu Asn Asp Gln Ser Pro Ser
 65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
            115                 120                 125

Glu Ser Asn Pro Pro Gln Val Leu Thr Thr Ser Tyr Gly Gln Asn Glu
        130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
    290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365

<210> SEQ ID NO 4
<211> LENGTH: 556
<212> TYPE: PRT
<213> ORGANISM: Trametes cingulata

<400> SEQUENCE: 4

Gln Ser Ser Ala Ala Asp Ala Tyr Val Ala Ser Glu Ser Pro Ile Ala
 1               5                  10                  15

Lys Ala Gly Val Leu Ala Asn Ile Gly Pro Ser Gly Ser Lys Ser Asn
                20                  25                  30
```

-continued

Gly Ala Lys Ala Gly Ile Val Ile Ala Ser Pro Ser Thr Ser Asn Pro
             35                  40                  45

Asn Tyr Leu Tyr Thr Trp Thr Arg Asp Ser Ser Leu Val Phe Lys Ala
 50                  55                  60

Leu Ile Asp Gln Phe Thr Thr Gly Glu Asp Thr Ser Leu Arg Thr Leu
 65                  70                  75                  80

Ile Asp Glu Phe Thr Ser Ala Glu Ala Ile Leu Gln Gln Val Pro Asn
                 85                  90                  95

Pro Ser Gly Thr Val Ser Thr Gly Leu Gly Glu Pro Lys Phe Asn
                100                 105                 110

Ile Asp Glu Thr Ala Phe Thr Asp Ala Trp Gly Arg Pro Gln Arg Asp
                115                 120                 125

Gly Pro Ala Leu Arg Ala Thr Ala Ile Ile Thr Tyr Ala Asn Trp Leu
130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Phe Phe Thr Thr Ala
                180                 185                 190

Val Gln His Arg Ala Leu Arg Glu Gly Ala Thr Phe Ala Asn Arg Ile
        195                 200                 205

Gly Gln Thr Ser Val Val Ser Gly Tyr Thr Thr Gln Ala Asn Asn Leu
        210                 215                 220

Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
                260                 265                 270

Phe Gln Pro Cys Ser Asp Lys Ala Leu Ser Asn Leu Lys Val Tyr Val
            275                 280                 285

Asp Ala Phe Arg Ser Ile Tyr Ser Ile Asn Ser Gly Ile Ala Ser Asn
        290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
                340                 345                 350

Ser Leu Pro Phe Phe Gln Gln Phe Ser Ser Gly Val Thr Val Gly Thr
            355                 360                 365

Tyr Ala Ser Ser Ser Ser Thr Phe Lys Thr Leu Thr Ser Ala Ile Lys
    370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
                420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Gly Ala Gly Thr Val Ala

```
                    450                 455                 460
Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
    530                 535                 540

Ala Ser Gly Thr Phe Thr Gln Asn Asp Thr Trp Arg
545                 550                 555

<210> SEQ ID NO 5
<211> LENGTH: 591
<212> TYPE: PRT
<213> ORGANISM: Talaromyces emersonii

<400> SEQUENCE: 5

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
50                  55                  60

Leu Val Asp Ala Phe Ile Ala Gly Asn Lys Asp Leu Glu Gln Thr Ile
65                  70                  75                  80

Gln Gln Tyr Ile Ser Ala Gln Ala Lys Val Gln Thr Ile Ser Asn Pro
                85                  90                  95

Ser Gly Asp Leu Ser Thr Gly Gly Leu Gly Glu Pro Lys Phe Asn Val
            100                 105                 110

Asn Glu Thr Ala Phe Thr Gly Pro Trp Gly Arg Pro Gln Arg Asp Gly
        115                 120                 125

Pro Ala Leu Arg Ala Thr Ala Leu Ile Ala Tyr Ala Asn Tyr Leu Ile
    130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270
```

```
Ser Ala Arg Ala Leu Ala Asn His Lys Val Val Thr Asp Ser Phe Arg
            275                 280                 285

Ser Ile Tyr Ala Ile Asn Ser Gly Ile Ala Glu Gly Ser Ala Val Ala
        290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
            325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
            405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ala Ser Ser Val Pro
            435                 440                 445

Ala Val Cys Ser Ala Thr Ser Ala Thr Gly Pro Tyr Ser Thr Ala Thr
        450                 455                 460

Asn Thr Val Trp Pro Ser Ser Gly Ser Gly Ser Ser Thr Thr Thr Ser
465                 470                 475                 480

Ser Ala Pro Cys Thr Thr Pro Thr Ser Val Ala Val Thr Phe Asp Glu
            485                 490                 495

Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
            515                 520                 525

Asp Ala Tyr Thr Asn Ser Asn Pro Leu Trp Tyr Val Thr Val Asn Leu
        530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Pro Asn Arg Ser Tyr Thr Val Pro
            565                 570                 575

Ala Tyr Cys Gly Gln Thr Thr Ala Ile Leu Asp Asp Ser Trp Gln
            580                 585                 590

<210> SEQ ID NO 6
<211> LENGTH: 555
<212> TYPE: PRT
<213> ORGANISM: Pynoporus sanguinea

<400> SEQUENCE: 6

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
            20                  25                  30

Gly Ala Lys Ala Gly Ile Val Val Ala Ser Pro Ser Thr Glu Asn Pro
        35                  40                  45

Asp Tyr Leu Tyr Thr Trp Thr Arg Asp Ser Ser Leu Val Phe Lys Leu
    50                  55                  60
```

```
Leu Ile Asp Gln Phe Thr Ser Gly Asp Thr Ser Leu Arg Gly Leu
 65                  70                  75                  80

Ile Asp Asp Phe Thr Ser Ala Glu Ala Ile Leu Gln Gln Val Ser Asn
                 85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
            115                 120                 125

Gly Pro Ala Leu Arg Ala Thr Ser Ile Ile Arg Tyr Ala Asn Trp Leu
130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
                180                 185                 190

Val Gln His Arg Ala Leu Arg Glu Gly Ala Thr Phe Ala Ser Arg Ile
            195                 200                 205

Gly Gln Ser Ser Val Val Ser Gly Tyr Thr Thr Gln Ala Asp Asn Leu
210                 215                 220

Leu Cys Phe Leu Gln Ser Tyr Trp Asn Pro Ser Gly Gly Tyr Val Thr
225                 230                 235                 240

Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
            275                 280                 285

Asp Ala Phe Arg Ser Ile Tyr Thr Ile Asn Asn Gly Ile Ala Ser Asn
290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
            355                 360                 365

Tyr Ser Ala Ser Ser Ser Thr Tyr Ala Thr Leu Thr Ser Ala Ile Arg
            370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
            435                 440                 445

Thr Val Pro Ala Ser Cys Ser Gly Gly Gly Ala Thr Val Ala Val
            450                 455                 460

Thr Phe Asn Val Gln Ala Thr Thr Val Phe Gly Glu Asn Ile Tyr Ile
465                 470                 475                 480
```

```
Thr Gly Ser Val Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
            515                 520                 525

Gln Val Thr Trp Glu Ser Asp Pro Asn Asn Gln Ile Thr Thr Pro Ser
            530                 535                 540

Gly Gly Ser Phe Thr Gln Asn Asp Val Trp Arg
545                 550                 555

<210> SEQ ID NO 7
<211> LENGTH: 556
<212> TYPE: PRT
<213> ORGANISM: Gloeophyllum sepiarium

<400> SEQUENCE: 7

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Ala Ser Pro Ser Thr Ser Asp Pro Asp Tyr
            35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Leu Gly Glu Pro Lys Phe Asn
            100                 105                 110

Val Asp Glu Thr Ala Phe Thr Gly Ala Trp Gly Arg Pro Gln Arg Asp
            115                 120                 125

Gly Pro Ala Leu Arg Ser Thr Ala Leu Ile Thr Tyr Gly Asn Trp Leu
    130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Ser Tyr Trp Asn Gln Ser Thr
                165                 170                 175

Tyr Asp Leu Trp Glu Glu Val Asp Ser Ser Ser Phe Phe Thr Thr Ala
            180                 185                 190

Val Gln His Arg Ala Leu Arg Glu Gly Ala Ala Phe Ala Thr Ala Ile
            195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
            245                 250                 255

Ala Ser Ile His Thr Tyr Asp Pro Ser Ala Gly Cys Asp Ala Ala Thr
            260                 265                 270

Phe Gln Pro Cys Ser Asp Lys Ala Leu Ser Asn Leu Lys Val Tyr Val
            275                 280                 285

Asp Ser Phe Arg Ser Val Tyr Ser Ile Asn Ser Gly Val Ala Ser Asn
            290                 295                 300
```

```
Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
            340                 345                 350

Ser Leu Ala Phe Phe Gln Gln Phe Ser Ser Gly Val Thr Ala Gly Thr
        355                 360                 365

Tyr Ser Ser Ser Ser Ser Thr Tyr Ser Thr Leu Thr Ser Ala Ile Lys
    370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
            420                 425                 430

Glu Ala Arg Asn Asn Thr Gln Phe Ala Gly Trp Gly Ala Ala Gly Leu
        435                 440                 445

Thr Val Pro Ser Ser Cys Ser Gly Asn Ser Gly Gly Pro Thr Val Ala
    450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
            500                 505                 510

Leu Pro Ala Ser Thr Ala Ile Glu Tyr Lys Tyr Ile Arg Lys Asn Asn
        515                 520                 525

Gly Ala Val Thr Trp Glu Ser Asp Pro Asn Asn Ser Ile Thr Thr Pro
    530                 535                 540

Ala Ser Gly Ser Thr Thr Glu Asn Asp Thr Trp Arg
545                 550                 555

<210> SEQ ID NO 8
<211> LENGTH: 559
<212> TYPE: PRT
<213> ORGANISM: Gloeophyllum trabeum

<400> SEQUENCE: 8

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
                20                  25                  30

Ala Ala Gly Val Val Ala Ser Pro Ser Lys Ser Asp Pro Asp Tyr
            35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
```

```
            115                 120                 125
Gly Pro Ala Leu Arg Ala Thr Ala Leu Ile Thr Tyr Gly Asn Trp Leu
            130                 135                 140
Leu Ser Asn Gly Asn Thr Thr Trp Val Thr Ser Thr Leu Trp Pro Ile
145                 150                 155                 160
Ile Gln Asn Asp Leu Asn Tyr Val Val Gln Tyr Trp Asn Gln Thr Thr
                165                 170                 175
Phe Asp Leu Trp Glu Glu Val Asn Ser Ser Phe Phe Thr Thr Ala
            180                 185                 190
Val Gln His Arg Ala Leu Arg Glu Gly Ala Ala Phe Ala Thr Lys Ile
            195                 200                 205
Gly Gln Thr Ser Ser Val Ser Ser Tyr Thr Thr Gln Ala Ala Asn Leu
            210                 215                 220
Leu Cys Phe Leu Gln Ser Tyr Trp Asn Pro Thr Ser Gly Tyr Ile Thr
225                 230                 235                 240
Ala Asn Thr Gly Gly Arg Ser Gly Lys Asp Ala Asn Thr Leu Leu
                245                 250                 255
Ala Ser Ile His Thr Tyr Asp Pro Ser Ala Gly Cys Asp Ala Thr Thr
            260                 265                 270
Phe Gln Pro Cys Ser Asp Lys Ala Leu Ser Asn Leu Lys Val Tyr Val
            275                 280                 285
Asp Ser Phe Arg Ser Val Tyr Ser Ile Asn Ser Gly Ile Ala Ser Asn
290                 295                 300
Ala Ala Val Ala Thr Gly Arg Tyr Pro Glu Asp Ser Tyr Gln Gly Gly
305                 310                 315                 320
Asn Pro Trp Tyr Leu Thr Thr Phe Ala Val Ala Glu Gln Leu Tyr Asp
                325                 330                 335
Ala Leu Asn Val Trp Ala Ala Gln Gly Ser Leu Asn Val Thr Ser Ile
            340                 345                 350
Ser Leu Pro Phe Phe Gln Gln Phe Ser Ser Ser Val Thr Ala Gly Thr
            355                 360                 365
Tyr Ala Ser Ser Ser Thr Thr Tyr Thr Thr Leu Thr Ser Ala Ile Lys
370                 375                 380
Ser Phe Ala Asp Gly Phe Val Ala Ile Asn Ala Gln Tyr Thr Pro Ser
385                 390                 395                 400
Asn Gly Gly Leu Ala Glu Gln Phe Ser Arg Ser Asn Gly Ala Pro Val
                405                 410                 415
Ser Ala Val Asp Leu Thr Trp Ser Tyr Ala Ser Ala Leu Thr Ala Phe
            420                 425                 430
Glu Ala Arg Asn Asn Thr Gln Phe Ala Gly Trp Gly Ala Val Gly Leu
            435                 440                 445
Thr Val Pro Thr Ser Cys Ser Ser Asn Ser Gly Gly Gly Gly Gly Ser
450                 455                 460
Thr Val Ala Val Thr Phe Asn Val Asn Ala Gln Thr Val Trp Gly Glu
465                 470                 475                 480
Asn Ile Tyr Ile Thr Gly Ser Val Asp Ala Leu Ser Asn Trp Ser Pro
                485                 490                 495
Asp Asn Ala Leu Leu Leu Ser Ser Ala Asn Tyr Pro Thr Trp Ser Ile
            500                 505                 510
Thr Val Asn Leu Pro Ala Ser Thr Ala Ile Gln Tyr Lys Tyr Ile Arg
            515                 520                 525
Lys Asn Asn Gly Ala Val Thr Trp Glu Ser Asp Pro Asn Asn Ser Ile
530                 535                 540
```

```
Thr Thr Pro Ala Ser Gly Ser Val Thr Glu Asn Asp Thr Trp Arg
545                 550                 555

<210> SEQ ID NO 9
<211> LENGTH: 583
<212> TYPE: PRT
<213> ORGANISM: Rhizomucor pusillus

<400> SEQUENCE: 9

Ala Thr Ser Asp Asp Trp Lys Gly Lys Ala Ile Tyr Gln Leu Leu Thr
1               5                   10                  15

Asp Arg Phe Gly Arg Ala Asp Asp Ser Thr Ser Asn Cys Ser Asn Leu
            20                  25                  30

Ser Asn Tyr Cys Gly Gly Thr Tyr Glu Gly Ile Thr Lys His Leu Asp
        35                  40                  45

Tyr Ile Ser Gly Met Gly Phe Asp Ala Ile Trp Ile Ser Pro Ile Pro
    50                  55                  60

Lys Asn Ser Asp Gly Gly Tyr His Gly Tyr Trp Ala Thr Asp Phe Tyr
65                  70                  75                  80

Gln Leu Asn Ser Asn Phe Gly Asp Glu Ser Gln Leu Lys Ala Leu Ile
                85                  90                  95

Gln Ala Ala His Glu Arg Asp Met Tyr Val Met Leu Asp Val Val Ala
            100                 105                 110

Asn His Ala Gly Pro Thr Ser Asn Gly Tyr Ser Gly Tyr Thr Phe Gly
        115                 120                 125

Asp Ala Ser Leu Tyr His Pro Lys Cys Thr Ile Asp Tyr Asn Asp Gln
    130                 135                 140

Thr Ser Ile Glu Gln Cys Trp Val Ala Asp Glu Leu Pro Asp Ile Asp
145                 150                 155                 160

Thr Glu Asn Ser Asp Asn Val Ala Ile Leu Asn Asp Ile Val Ser Gly
                165                 170                 175

Trp Val Gly Asn Tyr Ser Phe Asp Gly Ile Arg Ile Asp Thr Val Lys
            180                 185                 190

His Ile Arg Lys Asp Phe Trp Thr Gly Tyr Ala Glu Ala Ala Gly Val
        195                 200                 205

Phe Ala Thr Gly Glu Val Phe Asn Gly Asp Pro Ala Tyr Val Gly Pro
    210                 215                 220

Tyr Gln Lys Tyr Leu Pro Ser Leu Ile Asn Tyr Pro Met Tyr Tyr Ala
225                 230                 235                 240

Leu Asn Asp Val Phe Val Ser Lys Ser Lys Gly Phe Ser Arg Ile Ser
                245                 250                 255

Glu Met Leu Gly Ser Asn Arg Asn Ala Phe Glu Asp Thr Ser Val Leu
            260                 265                 270

Thr Thr Phe Val Asp Asn His Asp Asn Pro Arg Phe Leu Asn Ser Gln
        275                 280                 285

Ser Asp Lys Ala Leu Phe Lys Asn Ala Leu Thr Tyr Val Leu Leu Gly
    290                 295                 300

Glu Gly Ile Pro Ile Val Tyr Tyr Gly Ser Glu Gln Gly Phe Ser Gly
305                 310                 315                 320

Gly Ala Asp Pro Ala Asn Arg Glu Val Leu Trp Thr Thr Asn Tyr Asp
                325                 330                 335

Thr Ser Ser Asp Leu Tyr Gln Phe Ile Lys Thr Val Asn Ser Val Arg
            340                 345                 350

Met Lys Ser Asn Lys Ala Val Tyr Met Asp Ile Tyr Val Gly Asp Asn
```

```
            355                 360                 365
Ala Tyr Ala Phe Lys His Gly Asp Ala Leu Val Val Leu Asn Asn Tyr
370                 375                 380

Gly Ser Gly Ser Thr Asn Gln Val Ser Phe Ser Val Ser Gly Lys Phe
385                 390                 395                 400

Asp Ser Gly Ala Ser Leu Met Asp Ile Val Ser Asn Ile Thr Thr Thr
                405                 410                 415

Val Ser Ser Asp Gly Thr Val Thr Phe Asn Leu Lys Asp Gly Leu Pro
            420                 425                 430

Ala Ile Phe Thr Ser Ala Thr Gly Gly Thr Thr Thr Ala Thr Pro
                435                 440                 445

Thr Gly Ser Gly Ser Val Thr Ser Thr Ser Lys Thr Thr Ala Thr Ala
            450                 455                 460

Ser Lys Thr Ser Thr Ser Thr Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Thr Asp Thr Trp Arg
            580

<210> SEQ ID NO 10
<211> LENGTH: 515
<212> TYPE: PRT
<213> ORGANISM: Bacillus stearothermophilus

<400> SEQUENCE: 10

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140
```

```
Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 11
<211> LENGTH: 26
<212> TYPE: DNA
<213> ORGANISM: Artificial
<220> FEATURE:
<223> OTHER INFORMATION: PCR primer
```

```
<400> SEQUENCE: 11
agagcgauac catggtcgcc accagc                               26

<210> SEQ ID NO 12
<211> LENGTH: 28
<212> TYPE: DNA
<213> ORGANISM: Artificial
<220> FEATURE:
<223> OTHER INFORMATION: PCR primer

<400> SEQUENCE: 12
aacgtcacgu tcacaggccg accgcggt                             28
```